United States Patent [19]

Kamiya et al.

[11] Patent Number: 4,782,158

[45] Date of Patent: Nov. 1, 1988

[54] THIAZOLYLACETIC ACID DERIVATIVE

[75] Inventors: Takashi Kamiya, Suita; Kunihiko Tanaka, Toyonaka; Tsutomu Teraji, Osaka; Yoshiharu Nakai, Ohtsu, all of Japan

[73] Assignee: Fujisawa Pharmaceutical Co., Ltd., Osaka, Japan

[21] Appl. No.: 883,165

[22] Filed: Jul. 8, 1986

Related U.S. Application Data

[62] Division of Ser. No. 531,669, Sep. 13, 1983, Pat. No. 4,599,426, which is a division of Ser. No. 258,661, Apr. 29, 1981, Pat. No. 4,506,076, which is a division of Ser. No. 56,406, Jul. 11, 1979, Pat. No. 4,288,435.

[30] Foreign Application Priority Data

Jul. 17, 1978 [GB] United Kingdom ............... 30080

[51] Int. Cl.$^4$ ................. C07D 277/44; C07D 417/12
[52] U.S. Cl. .................................. 546/280; 548/194; 548/195; 548/119
[58] Field of Search ..................... 548/194; 546/280

[56] References Cited

U.S. PATENT DOCUMENTS 4,203,899 5/1980 Ochiai et al. .................. 548/194
4,278,793 7/1981 Durckheimer et al. ............ 548/194

Primary Examiner—Alan L. Rotman
Attorney, Agent, or Firm—Oblon, Fisher, Spivak, McClelland & Maier

[57] ABSTRACT

The present invention involves certain thiazol-4-yl-acetic acid compounds which are valuable intermediates for the preparation of cephem antibiotics. Said intermediates have the following structure:

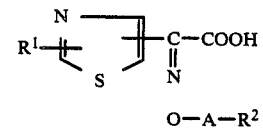

wherein $R^1$ is an amino or a protected amino group; $R^2$ is a group of the formula 13 CONH—$R^5$ or —NH-CO—$R^5$ wherein $R^5$ is pyridyl, thiazolyl or an isoxazolyl ring having lower alkyl and halogen substituted phenyl substituents, and A is lower alkylene, or a nontoxic salt thereof.

4 Claims, No Drawings

THIAZOLYLACETIC ACID DERIVATIVE

This is a divisional of co-pending application Ser. No. 531,669, filed Sept. 13, 1983, now U.S. Pat. No. 4,599,426, which is a divisional of Ser. No. 258,661, filed on Apr. 29, 1981, now U.S. Pat. No. 4,506,076, which is a divisional of Ser. No. 056,406, filed July 11, 1979, now U.S. Pat. No. 4,288,435.

The present invention relates to new 3,7-disubstituted-3-cephem-4-carboxylic acid compounds and pharmaceutically acceptable salts thereof. More particularly, it relates to new 3,7-disubstituted-3-cephem-4-carboxylic acid compounds and pharmaceutically acceptable salts thereof which have antimicrobial activities and to processes for preparation thereof, to pharmaceutical composition comprising the same, and to a method of using the same therapeutically in the treatment of infectious diseases in human being and animals.

Accordingly, it is one object of the present invention to provide 3,7-disubstituted-3-cephem-4-carboxylic acid compounds and pharmaceutically acceptable salts thereof, which are active against a number of pathogenic microorganisms.

Another object of the present invention is to provide processes for the preparation of 3,7-disubstituted-3-cephem-4-carboxylic acid compounds and pharmaceutically acceptable salts thereof.

A further object of the present invention is to provide pharmaceutical composition comprising, as active ingredients, said 3,7-disubstituted-3-cephem-4-carboxylic acid compounds and pharmaceutically acceptable salts thereof.

Still further object of the present invention is to provide a method for the treatment of infectious diseases caused by pathogenic bacteria in human being and animals.

The object 3,7-disubstituted-3-cephem-4-carboxylic acid compounds are novel and can be represented by the following general formula (I).

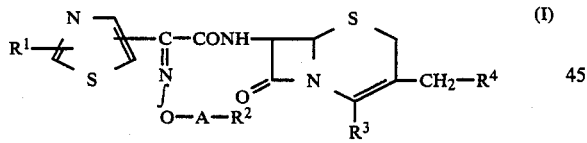

wherein
R$^1$ is amino or a protected amino group,
R$^2$ is a group of the formula: —CONH—R$^5$ (wherein R$^5$ is aryl which may have suitable substituent(s) or a heterocyclic group which may have suitable substituent(s)), a group of the formula:

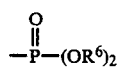

(wherein R$^6$ is hydrogen or lower alkyl) or a group of the formula: —NHCO—R$^5$ (wherein R$^5$ is as defined above),
R$^3$ is carboxy or a protected carboxy,
R$^4$ is acyloxy or a heterocyclicthio group which may have suitable substituent(s) and
A is lower alkylene.

According to the present invention, the 3,7-disubstituted-3-cephem-4-carboxylic acid compounds (I) can be prepared by various processes which are illustrated in the following schemes.

Process 1

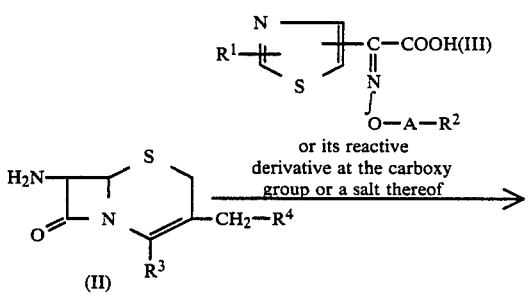

or its reactive derivative
at the amino group or a salt thereof

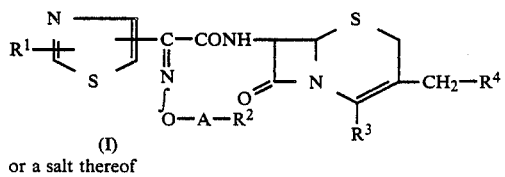

Process 2

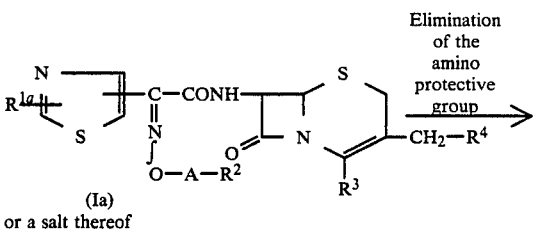

(Ia)
or a salt thereof

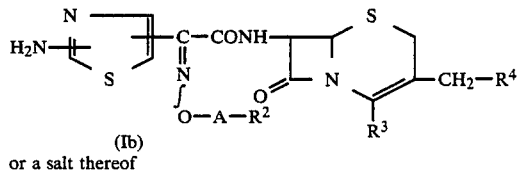

(Ib)
or a salt thereof

Process 3

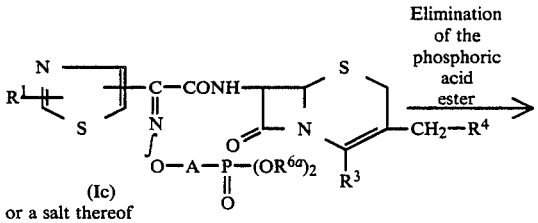

(Ic)
or a salt thereof

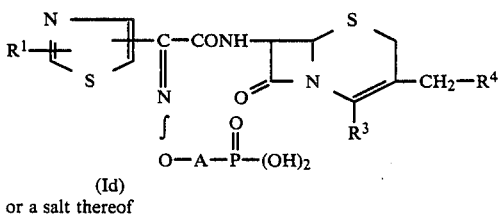

(Id)
or a salt thereof

Process 4

-continued

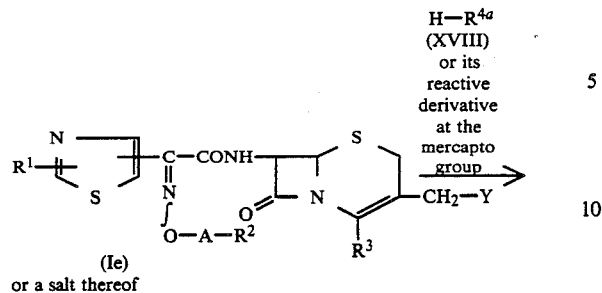

(Ie) or a salt thereof

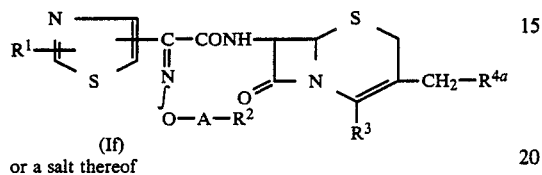

(If) or a salt thereof

Process 5

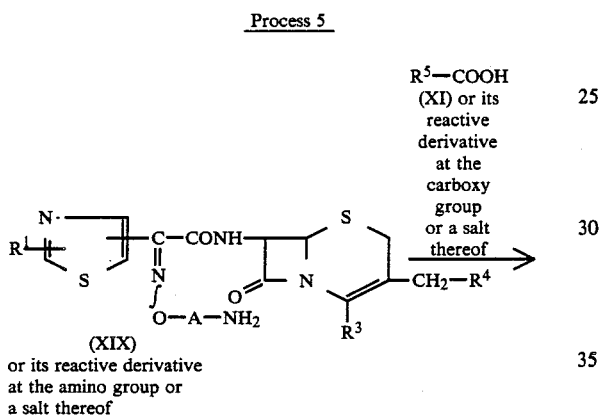

(XIX) or its reactive derivative at the amino group or a salt thereof

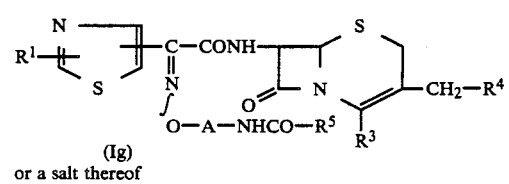

(Ig) or a salt thereof wherein
R$^1$, R$^2$, R$^3$, R$^4$, R$^5$ and A are each as defined above,
R$^{1a}$ is a protected amino,
R$^{4a}$ is a heterocyclicthio group which may have suitable substituent(s),
R$^{6a}$ is lower alkyl, and
Y is a group which can be substituted by a group of the formula: —R$^{4a}$ in which R$^{4a}$ is as defined above.

Among the starting compounds in the present invention, the compound (III) is novel and can be prepared by the process which are illustrated in the following schemes.

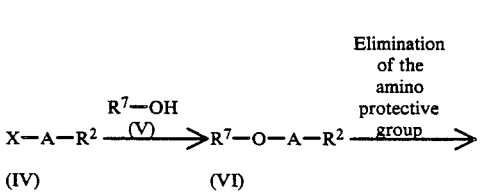

-continued

(VIII) or a salt thereof

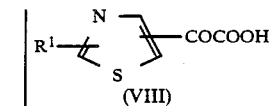

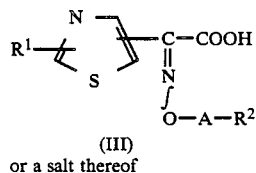

(III) or a salt thereof

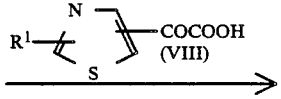

(IX) or a salt thereof

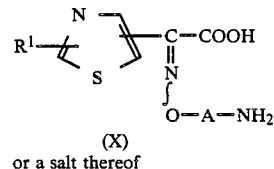

(X) or a salt thereof

R$^5$—COOH (XI) or its reactive derivative at the carboxy group or a salt thereof
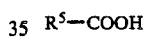

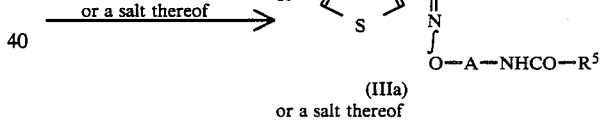

(IIIa) or a salt thereof

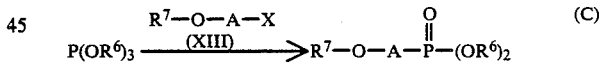

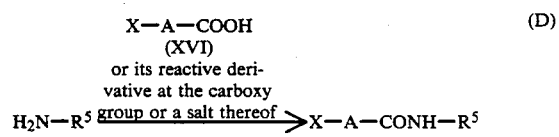

wherein
R$^1$, R$^2$, R$^5$, R$^6$ and A are each as defined above,
X is hydroxy or its reactive derivative, and
R$^7$ is amino having a protective group.

Regarding the object compounds (I), (Ia), (Ib), (Ic), (Id), (Ie), (If) and (Ig) and the starting compounds (III), (IIIa), (VIII), (X) and (XIX), it is to be understood that they include tautomeric isomers. That is, in case that the group of the formula:

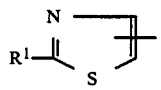

($R^1$ is as defined above) is contained in the molecules of said object and starting compounds, said group of the formula can also be alternatively represented by its tautomeric formula:

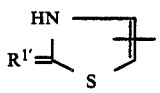

($R^{1'}$ is imino or a protected imino group). That is, the both of said groups are in the state of equilibrium each other and such tautomerism can be represented by the following equilibrium.

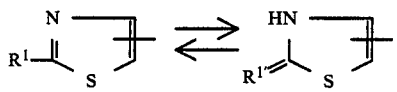

wherein $R^1$ and $R^{1'}$ are each as defined above.

These types of tautomerism between the amino-compound and the corresponding imino-compound as stated above have been well known in the literature, and it is obvious to a person skilled in the arts that both of the tautomeric isomers are easily convertible reciprocally and are included within the same category of the compound per se. Accordingly, the both of the tautomeric forms of the object compounds (I), (Ia), (Ib), (Ic), (Id), (Ie) (If) and (Ig) and the starting compounds (III), (IIIa) (VIII), (X) and (XIX) are clearly included within the scope of the present invention. In the present specification and claims, the object and starting compounds including the group of such tautomeric isomers are represented by using one of the expressions therefor, that is the formula:

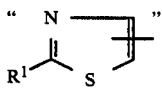

only for the convenient sake.

Furthermore, regarding the object compounds (I), (Ia), (Ib), (Ic), (Id), (Ie), (If) and (Ig) and the starting compounds (III), (IIIa), (X) and (XIX) it is to be understood that said object and starting compounds include syn isomer, anti isomer and a mixture thereof. For example, with regard to the object compound (I), syn isomer means one geometrical isomer having the partial structure represented by the following formula:

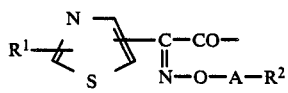

(wherein $R^1$, $R^2$ and A are each as defined above) and anti isomer means the other geometrical isomer having the partial structure represented by the following formula:

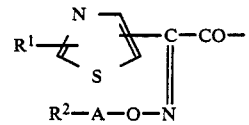

(wherein $R^1$, $R^2$ and A are each as defined above).

Regarding the other object and starting compounds as mentioned above, the syn isomer and the anti isomer can be also referred to the same geometrical isomers as illustrated for the compound (I).

Suitable pharmaceutically acceptable salts of the object compounds (I) are conventional non-toxic salt and include a metal salt such as an alkali metal salt (e.g., sodium salt, potassium salt, etc.) and an alkaline earth metal salt (e.g., calcium salt, magnesium salt, etc.), an ammonium salt, an organic base salt (e.g., trimethylamine salt, triethylamine salt, pyridine salt, picoline salt, dicyclohexylamine salt, N,N'-dibenzylethylenediamine salt, etc.), an organic acid salt (e.g., acetate, maleate, tartrate, methanesulfonate, benzenesulfonate, formate, toluenesulfonate, etc.), an inorganic acid salt (e.g., hydrochloride, hyrobromide, sulfate, phosphate, etc.), or a salt with an amino acid (e.g., arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable protected amino for $R^1$ may include an acylamino or an amino group substituted by a conventional protecting group such as ar(lower)alkyl which may have at least one suitable substituent(s), (e.g., benzyl, trityl, etc.) or the like.

Suitable acyl moiety in the terms "acylamino" and "acyloxy" for $R^4$ may include carbamoyl, aliphatic acyl group and acyl group containing an aromatic or heterocyclic ring. And, suitable examples of the said acyl may be lower alkanoyl (e.g., formyl, acetyl, propionyl, butyryl, isobutyryl, valeryl, isovaleryl, oxalyl, succinyl, pivaloyl, etc.);

lower alkoxycarbonyl (e.g., methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.);

lower alkanesulfonyl (e.g., mesyl, ethanesulfonyl, propanesulfonyl, isopropanesulfonyl, butanesulfonyl, etc.);

arenesulfonyl (e.g., benzenesulfonyl, tosyl, etc.); aroyl (e.g., benzoyl, toluoyl, xyloyl, naphthoyl, phthaloyl, indancarbonyl, etc.);

ar(lower)alkanoyl (e.g., phenylacetyl, phenylpropionyl, etc.);

ar(lower)alkoxycarbonyl (e.g., benzyloxycarbonyl, phenethyloxycarbonyl, etc.), and the like.

The acyl moiety as stated above may have at least one suitable sustituent(s) such as halogen (chlorine, bromine, fluorine and iodine) or the like.

Preferable examples of acylamino and acyloxy groups may include lower alkanoylamino and lower alkanoyloxy, respectively.

The aryl groups in the term "aryl which may have suitable substituent(s)" may include phenyl, tolyl, xylyl mesityl, cumenyl, naphthyl and the like. These groups may have one or more suitable substituent(s) such as halogen, hydroxy, carboxy, esterified carboxy as mentioned below or the like. In case that said aryl groups have two or more substituents, the substituents may be the same or different.

The heterocyclic moiety in the terms "heterocyclic group which may have suitable substituent(s)" and "heterocyclicthio group which may have suitable substituent(s)" means saturated or unsaturated, monocyclic or polycyclic heterocyclic group containing at least one hetero-atom such as an oxygen, sulfur, nitrogen atom and the like. And, especially preferable heterocyclic group may be heterocyclic group such as unsaturated 3 to 8-membered heteromonocyclic group containing 1 to 4 nitrogen atom(s) for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered heteromonocyclic group containing 1 to 4 nitrogen atom(s), for example, pyrrolidinyl, imidazolidinyl, piperidino, piperazinyl, etc.;

unsaturated condensed heterocyclic group containing 1 to 4 nitrogen atom(s), for example, indolyl, isoindolyl, indolizynyl, benzimidazolyl, quinolyl, isoquinolyl, indazolyl, benzotriazolyl, etc.;

unsaturated 3 to 8-membered heteromonocyclic group containing 1 to 2 oxygen atom(s) and 1 to 3 nitrogen atom(s), for example, oxazolyl, isoxazolyl, oxadiazolyl, (e.g. 1,2,4-oxadiazolyl, 1,3,4-oxadiazolyl, 1,2,5-oxadiazolyl, etc.) etc.;

saturated 3 to 8-membered heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered heteromonocyclic group containing 1 to 2 sulfur atom(s) and 1 to 3 nitrogen atom(s), for example, thiazolidinyl, etc.;

unsaturated 3 to 8 membered heteromonocyclic group containing 1 to 2 sulfur atom(s), for example, thienyl, dihydrodithiinyl, dihydrodithiolyl, etc.;

unsaturated condensed heterocyclic group containing 1 to 2 sulfur atom(s) and 1 to 3 nitrogen atom(s), for example, benzothiazolyl benzothiadiazolyl, etc.;

unsaturated 3 to 8-membered heteromonocyclic group containing an oxygen atom, for example, furyl, etc.;

unsaturated 3 to 8-membered heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

The heterocyclic moieties as mentioned above may have at least one substituent(s) such as lower alkyl mentioned below, di(lower)alkylamino(lower)alkyl (.e.g, dimethylaminomethyl, dimethylaminoethyl, diethylaminopropyl, diethylaminobutyl, etc.), lower alkenyl (e.g., vinyl, allyl, butenyl, etc.), aryl which may have suitable substituent(s) as defined above, hologen mentioned below, amino(lower)alkyl (e.g., aminomethyl, aminoethyl, etc.), carboxy(lower)alkyl (e.g., carboxymethyl, carboxyethyl, etc.), amino or the like.

Preferable example of heterocyclic moieties having suitable substituent(s) may include tetrazolyl having lower alkyl (e.g., methyltetrazolyl, ethyltetrazolyl, etc.), thiadiazolyl having lower alkyl (e.g., methylthiadiazolyl, ethylthiadiazolyl, etc.) and isoxazolyl having lower alkyl and halogen substituted aryl (e.g., 5-methyl-3-chlorophenylisoxazolyl, 5-methyl-3-bromophenylisoxazolyl, 5-ethyl-3-chlorophenylisoxazolyl, etc.).

Suitable lower alkyl means straight or branched one and may include methyl, ethyl, propyl, isopropyl, butyl, isobutyl, tert-butyl, pentyl, hexyl and the like.

Suitable protected carboxy may include an esterified carboxy and the like, and suitable examples of the ester moiety in said esterified carboxy may be the ones such as lower alkyl ester (e.g., methyl ester, ethyl ester, propyl ester, isopropyl ester, butyl ester, isobutyl ester, pentyl ester, hexyl ester, 1-cyclopropylethyl ester, etc.) which may have at least one suitable substituent(s), for example, lower alkanoyloxy(lower)alkyl ester (e.g., acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, hexanoyloxymethyl ester, etc.), lower alkanesulfonyl(lower)alkyl ester (e.g., 2-mesylethyl ester, etc.) or mono(or di or tri)-halo(lower-)alkyl ester (e.g., 2-iodoethyl ester, 2,2,2-trichloroethyl ester, etc); lower alkenyl ester (e.g., vinyl ester, allyl ester, etc.);

lower alkynyl ester (e.g., ethynyl ester, propynyl ester, etc.);

ar(lower)alkyl ester which may have at least one suitable substituent(s) (e.g., benzyl ester, 4-methoxybenzyl ester, 4-nitrobenzyl ester, phenethyl ester, trityl ester, diphenylmethyl ester, bis(methoxyphenyl)-methyl ester, 3,4-dimethoxybenzyl ester, 4-hydroxy-3,5-ditertiarybutylbenzyl ester, etc.);

aryl ester which may have at least one suitable substituent(s) (e.g., phenyl ester, 4-chlorophenyl ester, tolyl ester, tetriarybutylphenyl ester, xylyl ester, mesityl ester, cumenyl ester, etc.), and the like.

Preferable example of the esterified carboxy as mentioned above may include lower alkoxycarbonyl (e.g., methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.).

Suitable lower alkylene means straight or branched one and may include methylene, ethylene, trimethylene, propylene, tetramethylene, pentamethylene, hexamethylene and the like.

Suitable hydroxy reactive derivative for X may include an acid residue such as halogen as mentioned above or the like.

Suitable amino having a protective group for $R^7$ may include phthalimido, succinimido, ethoxycarbonylamino and the like, and preferably phthalimido.

Suitable example of a group which can be substituted by a group of the formula: $-R^{4a}$ may include an acid residue (e.g., azido, aforesaid halogen, acyloxy, etc. and the like.

The preferable examples of the object compound (I) are exemplified as follows.

Preferable example of $R^1$ is amino or lower alkanoylamino; $R^2$ is a group of the formula: $-CONH-R^5$ [wherein preferable example of $R^5$ is aryl group having at least one substituent(s), which may be the same or different, such as halogen, hydroxy, carboxy or lower alkoxycarbonyl (more preferably, phenyl having at least one substituent(s) as mentioned above); pyridyl or thiazolyl], a group of the formula:

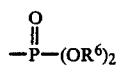

(wherein preferable example of $R^6$ is hydrogen or lower alkyl) or a group of the formula: $-NHCO-R^5$ [wherein preferable example of $R^5$ is aryl (more preferably, phenyl) having hydroxy and halogen as substituents or isoxazolyl having lower alkyl and halogen substituted aryl as substituents (more preferably, isoxazolyl having lower alkyl and halogen substituted phenyl)]; $R^3$ is carboxy; $R^4$ is lower alkanoyloxy, tetrazolylthio which may have lower alkyl group, thiadiazolylthio which may have lower alkyl group as substituent, or benzothiazolylthio; and A is lower alkylene.

The processes for preparing the object compounds of the present invention are explained in details in the following.

Process 1:

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as acetoacetic acid or the like; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g., benzoic acid, etc.); a symmetrical acid anhydride; an activated amide with imidazole, 4-substituted imidazole, dimethylpyrazole, triazole or tetrazole; or an activated ester (e.g., cyanomethyl ester, methoxymethyl ester, dimethyliminomethyl [$(CH_3)_2\overset{+}{N}=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester p-cresyl thioester, carboxymethyl thioester, pyranyl ester, pyridyl ester, piperidyl ester, 8-quinolyl thioester, etc.), or an ester with a N-hydroxy compound (e.g., N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonyl-bis-(2-methyl imidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride; phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

In the present reaction, a syn isomer of the object compound (I) can be obtained preferably by conducting the present reaction of the compound (II) with the corresponding syn isomer of the starting compound (III), for example, in the presence of a Vilsmeier reagent as mentioned above etc. and under around neutral condition.

Process 2:

The object compound (Ib) or a salt thereof can be prepared by subjecting the compound (Ia) or a salt thereof to elimination reaction of the amino protective group.

Suitable salt of the compound (Ia) can be referred to the metal salt, ammonium salt and organic amine salt exemplified for the compound (II).

The elimination reaction is carried out in accordance with a conventional method such as hydrolysis; reduction; a method treating the compound (Ia) wherein $R^{1a}$ is acylamino with iminohalogenating agent, iminoetherifying agent and then, if necessary, hydrolyzing the resultant; or the like. The hydrolysis may include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, for example, tert-pentyloxycarbonyl, lower alkanoyl (e.g., formyl, acetyl, etc.), cycloalkoxycarbonyl, substituted or unsubstituted aralkoxycarbonyl, aralkyl (e.g., trityl), substituted phenylthio, substituted aralkylidene, substituted alkylidene, substituted cycloalkylidene or the like.

Suitable acid includes an organic or inorganic acid such as formic acid, trifluoroacetic acid, benenesulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, hydrochloric acid, etc. The acids can be selected according to the kind of the protective group to be eliminated. When the elimination reaction is conducted with an acid it can be carried out in the presence or absence of a solvent. Suitable solvent includes water, a conventional organic solvent or a mixture thereof.

The elimination reaction using trifluoroacetic acid may be carried out in the presence of anisole. The hydrolysis using hydrazine is commonly applied for eliminating a phthaloyl, succinyl type amino-protective group.

The elimination using base is used for eliminating an acyl group such as trifluoroacetyl. Suitable base may include an inorganic base and an organic base.

The reductive elimination is generally applied for eliminating the protective group, for example, haloalkoxycarbonyl (e.g., trichloroethoxycarbonyl, etc.), substituted or unsubstituted aralkoxy carbonyl(e.g., benzyloxycarbonyl, etc.), 2-pyridylmethoxycarbonyl, etc. Suitable reduction may include, for example, reduction with an alkali metal borohydride (e.g., sodium borohydride, etc.), reduction with a combination of a metal (e.g., tin, zinc, iron, etc.) or the said metal together with a metal salt compound (e.g., chromous chloride, chromous acetate, etc.) and an organic or inorganic acid (e.g., acetic acid, propionic acid, hydrochloric acid, etc.); and catalytic reduction. Suitable catalyst includes a conventional one, for example, Raney nickel, platinum oxide, palladium on charcoal and the like.

Among the protective groups, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g., phosphorus oxychloride, etc.) and an iminoetherifying agent such as lower alkanol (e.g., methanol, ethanol, etc.), if necessary, followed by hydrolysis.

The reaction temperature is not critical and may suitably be selected in accordance with the kind of the protective group for the amino group and the elimination method as mentioned above, and the reaction is preferably carried out under a mild condition such as under cooling or at slightly elevated temperature.

The present invention includes, within its scope, the cases that an esterified carboxy being a substituent on aryl for $R^5$ is transformed into the free carboxy group and a protected carboxy for $R^3$ is transformed into the free carboxy group according to the reaction conditions and/or kinds of the carboxy protective group during the reaction or the post-treating step of the present process.

Process 3:

The object compound (Id) or a salt thereof can be prepared by subjecting a compound (Ic) or a salt thereof to the elimination reaction of phosphoric acid ester.

Suitable salts of the compound (Ic) can be referred to the ones exemplified for the compound (Ia).

This elimination reaction can be conducted, for example, by reacting a compound (Ic) or a salt thereof with a trialkylsilyl halide (e.g. trimethylsilyl bromide, trimethylsilyl iodide, trimethylsilylchloride, etc.), preferably in the presence of a silylating agent such as bis(trimethylsilyl)acetamide, trimethylsilylacetamide and the like.

The reaction is preferably carried out in a solvent such as methylene chloride or any other organic ones which do not adversely influence the reaction. The reaction temperature is not critical and the reaction is usually carried out under relatively mild conditions such as around ambient temperature.

The present invention includes, within its cope, the case that a protected amino for $R^1$ is converted into the free amino group according to reaction conditions and/or kinds of the amino protective group during the reaction or the posttreating step of the present process.

Process 4:

The object compound (If) or a salt thereof can be prepared by reacting a compound (Ie) or a salt thereof with a compound (XVIII) or its reactive derivative at the mercapto group.

Suitable salts of the compound (Ie) are referred to the ones exemplified for the compound (I).

Suitable reactive derivative at the mercapto group in the compound (XVIII) may include a metal salt such as an alkali metal salt (e.g. sodium salt, potassium salt, etc.), an alkaline earth metal salt (e.g., magnesium salt, etc.) or the like.

The reaction is usually carried out in a solvent such as water, acetone, chloroform, nitrobenzene, methylene chloride, ethylene chloride, dimethylformamide, methanol, ethanol, ether, tetrahydrofuran or any other conventional solvents which do not adversely influence the reaction, preferably in ones having strong polarity, which may be used as a mixture with water.

When the compound (Ie) and/or the compound (XVIII) are used in free form in the reactions, the reaction is preferably carried out in the presence of a base, for example, an organic or an inorganic base such as alkali metal hydroxide, alkali metal carbonate, alkali metal bicarbonate, trialkylamine, pyridine or the like, and preferably carried out around neutral conditions. The reaction temperature is not critical and the reaction is usually carried out at ambient temperature or under warming.

The present invention includes, within its scope, the cases that a protected amino and/or a protected carboxy group are converted into the corresponding free amino and/or the free carboxy group during the reaction or the post-treating step of the present process.

Process 5:

The object compound (Ig) or a salt thereof can be prepared by reacting the compound (XIX) or its reactive derivative at the amino group or a salt thereof with the compound (XI) or its reactive derivative at the carboxy group or a salt thereof.

Suitable reactive derivative at the amino group and salts of the compound (XIX) can be referred to the ones exemplified for the compound (II).

Suitable reactive derivative at the carboxy group and salts of the compound (XI) can be referred to the ones exemplified for the compound (III).

The present reaction is carried out substantially in the same manner as illustrated in Process 1.

Processes for the preparation of the starting compounds (III) are explained in detail as follows.

Preparation 1, (IV)+(V)→(VI): [Process (A)]

The compound (VI) can be prepared by reacting a compound (IV) with a compound (V).

The reaction is preferably carried out in the presence of a base as exemplified in Process 1 in case that X is an acid residue and in the presence of a condensing agent, for example, one formed by triphenylphosphine and diethyl azoformate in case that X is hydroxy, respectively.

The reaction is usually carried out in a solvent such as acetonitrile, dimethylformamide, tetrahydrofuran or any other solvents which do not adversely influence the reaction. The reaction temperature is not critical and the reaction is usually carried out from cooling to heating around a boiling point of the solvent used.

Preparation 2. (VI)→(VII): [Process (A)]

The compound (VII) or a salt thereof can be prepared by subjecting a compound (VI) to elimination reaction of the amino protective group.

This elimination reaction of the amino protective group of the compound (VI) can be carried out in a similar manner to that of aforementioned Process 2.

Suitable solvents include water, ethanol, chloroform, diethyl ether and the like. The reaction temperature is not critical and the reaction is usually carried out under warming or heating.

Preparation 3. (VII)+(VIII)→(III): [Process (A)]

The compound (III) or a salt thereof can be prepared by reacting a compound (VII) or a salt thereof with a compound (VIII).

Suitable salts of the compound (VII) include an inorganic acid salt (e.g., hydrochloride, hydrobromide, sulfate, etc.), an organic acid salt (e.g., acetate, p-toluenesulfonate, etc.) and the like.

The reaction is usually carried out in a conventional solvent such as water, alcohol (e.g., methanol, ethanol, etc.), a mixture thereof or any other ones which do not adversely influence the reaction.

When the compound (VII) is used in its salt form, the reaction is preferably carried out in the presence of an organic or an inorganic base as exemplified before.

The reaction temperature is not critical, and the reaction is usually carried out from cooling to heating.

In the present reaction, a syn isomer of the compound (III) can be obtained preferably by conducting the present reaction under around neutral conditions.

Preparation 4. (IX)+(VIII)→(X): [Process (B)]

The compound (X) or a salt thereof can be prepared by reacting a compound (IX) or a salt thereof with a compound (VIII).

Suitable salts of the compound (IX) can be referred to the ones as exemplified for the compound (VII).

This reaction is carried out in a similar manner to that of Preparation 3 [(VII)+(VIII)→(III)].

Preparation 5. (X)+(XI)→(IIIa) [Process (B)]

The compound (IIIa) or a salt thereof can be prepared by reacting a compound (X) or a salt thereof with a compound (XI) or its reactive derivative at the carboxy group or salt thereof.

Suitable salts of the compound (X) can be referred to the ones exemplified for the compound (III) and suitable reactive derivative at the carboxy group and salts of the compound (XI) can be referred to the ones exemplified for the compound (III), respectively.

The present reaction is carried out in a similar manner to that of aforesaid Process 1.

Preparation 6. (XII)+(XIII)→(XIV): [Process (C)]

The compound (XIV) can be prepared by reacting a compound (XII) with a compound (XIII).

The present reaction can be carried out even in the absence of a solvent. The reaction temperature is not critical and the reaction is usually carried out under heating.

Preparation 7. (XV)+(XVI)→(XVII): [Process (D)]

The compound (XVII) can be prepared by reacting a compound (XV) or a salt thereof with a compound (XVI) or its reactive derivative at the carboxy group or a salt thereof.

Suitable salts of the compound (XV) can be referred to the ones exemplified for the compound (VII) and suitable reactive derivative at the carboxy group and salt of the compound (XVI) can be referred to the ones exemplified for the compound (III), respectively.

This reaction is carried out in a similar manner to that of aforementioned Process 1.

The present invention includes, within its scope, the cases that the one type of tautomeric isomers is converted into the other type of isomer during the reaction and/or the post-treating step of the each process.

In case that the object compound (I) is obtained in a form of the free acid at the 4-position and/or in case the compound (I) has free amino group, it may be transformed into its pharmaceutically acceptable salt as aforementioned by a conventional method.

The object compounds (I) and pharmaceutically acceptable salt thereof of the present invention are novel compounds which exhibit high antibacterial activity and inhibit the growth of a wide variety of pathogenic microorganisms including Gram-positive and Gram-negative bacteria. For therapeutic purpose, the compounds according to the present invention can be used in the form of pharmaceutical preparation which contain said compounds, as an active ingredient, in admixture with a pharmaceutically acceptable carriers such as an organic or inorganic solid or liquid excipient suitable for oral, parenteral or external administration. The pharmaceutical preparations may be capsules, tablets, dragees, ointments or suppositories, solutions, suspensions, emulsions, and the like. If desired, there may be included in the above preparations auxiliary substances, stabilizing agents wetting or emulsifying agents, buffers and other commonly used additives.

While the dosage of the compounds will vary depend upon the age and condition of the patient, an average single dose of about 10 mg., 50 mg., 100 mg., 250 mg., 500 mg., and 1000 mg. of the compounds according to the present invention was proved to be effective for treating infectious diseases caused by pathogenic bacteria. In general, amounts between 1 mg/body and about 6,000 mg/body or even more may be administered per day.

In order to illustrate the usefulness of the object compounds, anti-microbial activities of some respresentative compounds of the present invention against some test strains of pathogenic bacteria are shown in their minimal inhibitory concentrations below.

Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of μg/ml. after incubation at 37° C. for 20 hours.

Test compounds (1) 7-[2-{N-(2-Hydroxy-5-chlorophenyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer)
(2) 7-[2-(2-Phosphonoethoxyimino)-2-(2-aminothiazol-4-yl)acetamido]-3-(1-methyl-1H-tetrazol-5-yl)thiomethyl-3-cephem-4-carboxylic acid (syn isomer)
(3) 7-[2-Phosphonomethoxyimino-2-(2-aminothiazol-4-yl)acetamido]-3-(1-methyl-1H-tetrazol-5-yl)thiomethyl-3-cephem-4-carboxylic acid (syn isomer).
(4) 7-[2-{N-(3-Pyridyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer).

Test result

| Test Microorganism | M.I.C. (μg/ml) | | | |
| --- | --- | --- | --- | --- |
| | Compound (1) | Compound (2) | Compound (3) | Compound (4) |
| Proteus vulgaris IAM-1025 | 6.25 | 0.025 | 0.10 | 0.39 |
| Pseudomonas aeruginosa NCTC-10490 | 6.25 | 25 | 3.13 | 3.13 |
| Pseudomonas aeruginosa 721 | 12.5 | 25 | 6.25 | 6.25 |
| Proteus mirabilis 501 | 0.78 | 0.0125 | 0.025 | 0.39 |

The following Preparations and Examples are given for the purpose of illustrating the present invention.

Preparation of the starting compound

PREPARATION 1

(1) Preparation of N-(2-Hydroxy-5-chlorophenyl)-2-bromoacetamide

To a mixture of 2-amino-4-chlorophenol (19.50 g.) and N,N-dimethylaniline (19.90 g.) in dry acetone (200 ml.) was added dropwise bromoacetyl bromide (33.2 g.) over a period of 15 minutes under ice-cooling at below 10° C. with stirring and stirring was continued for 45 minutes at the same temperature. The reaction mixture was evaporated and to the residue were added ethyl acetate and water. The ethyl acetate layer was washed with 5% hydrochloric acid (twice), water, 5% aqueous solution of sodium bicarbonate, water (twice) and a saturated aqueous solution of sodium chloride successively, dried over magnesium sulfate, treated with activated charcoal and then evaporated. The residue was recrystallized from a mixture of ethyl acetate and diisopropyl ether to give the title compound (18.91 g.).

I.R. (Nujol): 3390, 3150, 1650 cm$^{-1}$
N.M.R. (DMSO-d$_6$, δ): 4.22 (2H, s), 6.8–7.2 (2H, m), 8.05 (1H, d, J=2 Hz)

(2) Preparation of N-(2-Hydroxy-5-chlorophenyl)-2-(phthalimidoxy)acetamide

To a mixture of N-hydroxyphthalimide (10.84 g.) and triethylamine (6.72 g.) in dry acetonitrile (160 ml.) was added N-(2-hydroxy-5-chlorophenyl)-2-bromoacetamide (17.6 g.) with stirring under ice-cooling and stirring was continued for 1.5 hours at room temperature. The precipitates were separated from the reaction mixture by filtration, washed successively with acetonitrile, ethyl acetate and water to give the title compound (18.4 g.).

I.R. (Nujol): 3400, 3100, 1800, 1740, 1660 cm$^{-1}$
N.M.R. (DMSO-d$_6$+D$_2$O, δ): 4.92 (2H, s), 6.9–7.1 (2H, m), 7.90 (4H, s), 8.08 (1H, d, J=2 Hz)

(3) N-(2-Hydroxy-5-chlorophenyl)-2-(aminooxy)acetamide

A mixture of N-(2-hydroxy-5-chlorophenyl)-2-(phthalimidoxy)acetamide (10.0 g.) and hydrazine.hydrate (1.442 g.) in ethanol (100 ml.) was refluxed under heating for 2 hours. After allowing the reaction mixture to stand under ice-cooling, the preciptates were separated by filtration and washed with ethanol. The combined filtrate and washed was evaporated and to the residue was added ethyl acetate. After removal of insoluble substances by filtration, the filtrate was extracted with 5% hydrochloric acid. The extract was washed with ethyl acetate, adjusted to about pH 7 with an aqueous solution of sodium bicarbonate and then reextracted with ethyl acetate. The ethyl acetate extract was washed with an aqueous solution of sodium chloride, dried over magnesium sulfate and then evaporated to give crystals of the title compound (4.59 g.).

I.R. (Nujol): 3330, 3260, 1690 cm$^{-1}$
N.M.R. (DMSO-d$_6$+D$_2$O, δ): 4.20 (2H, s), 6.9–7.1 (2H, m), 8.1–8.2 (1H, m)

(4)

2-[N-(2-Hydroxy-5-chlorophenyl)carbamoylmethoxyimino]-2-(2-formamidothiazol-4-yl)acetic acid (syn isomer)

A mixture of 2-(2-formamidothiazol-4-yl)glyoxylic acid (2.79 g.) and N-(2-hydroxy-5-chlorophenyl)-2-(aminooxy)acetamide (3.32 g.) in ethanol (30 ml.) was stirred for 5 hours at room temperature. The reaction mixture was evaporated to dryness and to the residue was added a mixture of ethyl acetate, water and 10% hydrochloric acid followed by stirring. The ethyl acetate layer was separated, washed with diluted hydrochloric acid and an aqueous solution of sodium chloride, dried over magnesium sulfate, concentrated to a small volume and allowed to stand under ice-cooling. The resulting precipitates were collected by filtration, washed with ethyl acetate and then dried under reduced pressure to give a title compound (4.59 g.).

I.R. (Nujol): 3300, 1735, 1695, 1649 cm$^{-1}$

N.M.R. (DMSO-$d_6$+$D_2O$, δ): 4.83 (2H, s), 6.8–7.2 (2H, m), 7.63 (1H, s), 8.15 (1H, d, J=2 Hz), 8.55 (1H, s)

PREPARATION 2

(1) Preparation of Diethyl (phthalimidoxymethyl)phosphonate

To a mixture of diethyl hydroxymethylphosphonate (18.4 g.), N-hydroxyphthalimide (12.6 g.) and triphenylphosphine (28.8 g.) in tetrahydrofuran (270 ml.) was added dropwire diethyl azoformate (21.0 g.) under ice-water cooling followed by stirring at room temperature overnight. The reaction mixture was evaporated and to the residue was added diethyl ether (300 ml.) followed by stirring for 30 minutes under ice-cooling. The resulting mixture was filtered to remove insoluble substances and the filtrate was concentrated.

The residue was chromatographed on silica gel (600 g.) using a mixture of benzene and ethyl acetate (1:1) as an eluent. Fractions containing a mixture of the desired compound and triphenylphosphineoxide were evaporated to dryness and to the residue was added diethyl ether. The resulting mixture was filtered to remove insoluble materials and then evaporated to give the crude title compound (19.0 g.).

N.M.R. (CDCl$_3$, δ): 2.36 (6H, t, J=7 Hz), 4.25 (4H, d, t, J=14, 7 Hz), 4.56 (2H, d, J=10 Hz), 7.2–7.9 (13H, m)

Thus obtained product was used in the next step reaction without further purification.

(2) Preparation of Diethyl (aminooxymethyl)phosphonate

A mixture of diethyl (phthalimidoxymethyl)phosphonate (14.48 g.) and hydrazine hydrate (2.32 g.) in ethanol (130 ml.) was refluxed under heating for 2 hours. After cooling, the reaction mixture was filtered to separate insoluble substances, which were washed with ethanol. The combined filtrate and washing was concentrated after addition of chloroform to the concentrate, the resulting mixture was filtered to remove insoluble substances, which were washed with chloroform. The combined filtrate and washing was again concentrated and then the concentrate was dissolved in ethyl acetate. To the ethyl acetate solution were added water and 10% hydrochloric acid followed by shaking (so that the pH became about 2) and separation of ethyl acetate layer. After repeating these operations twice, the remaining aqueous layers were combined, washed with ethyl acetate, adjusted to pH about 4 with an aqueous solution of sodium bicarbonate and then concentrated under reduced pressure (the weight of the concentrate: about 25 g.). There was obtained the concentrate containing the title compound. Thus obtained concentrate was used directly in the next step reaction.

(3) Preparation of 2-(O,O-Diethylphosphino)methoxyimino-2-(2-formamidothiazol-4-yl)acetic acid (syn isomer)

To the concentrate containing diethyl (aminooxymethyl)phosphonate obtained in Preparation 2-(2) were added ethanol (80 ml.) and 2-(2-formamidothiazol-4-yl)glyoxylic acid (5.80 g.) followed by stirring for an hour at room temperature. The reaction mixture was adjusted to pH about 7 with a saturated aqueous solution of sodium bicarbonate and evaporated. After addition of a small amount of water to the residue, the resulting mixture was washed with ethyl acetate, and then adjusted to pH 2 with 10% hydrochloric acid whereby an oil substance had formed, which was extracted with ethyl acetate. The extract was washed with a small amount of water, dried over magnesium sulfate, treated with activated charcoal and then evaporated to give the foamy title compound (9.35 g.).

I.R. (K Br): 1740, 1700 cm$^{-1}$

N.M.R. (CDCl$_3$, δ): 1.33 (6H, t, J=7 Hz), 4.27 (4H, d, t, J=15, 7 Hz), 4.70 (2H, d, J=7 Hz), 7.43 (1H), s), 8.70 (1H, s)

PREPARATION 3

(1) Preparation of Diethyl(2-Phthalimidoxyethyl)phosphonate

A mixture of N-(2-bromoethoxy)phthalimide (2.0 g.) and triethylphosphite (2.46 g.) was stirred for 4 hours at 155° to 160° C. After removal of excess triethylphosphite from the reaction mixture, an oily residue was dissolved in ethyl acetate. This solution was washed successively with water, an aqueous solution of sodium bicarbonate and water, dried and then evaporated to give an oil (3.3 g.), which was chromatographed on silica gel (90 g.) using ethyl acetate as an eluent to give the title compound (0.9 g.).

I.R. (Nujol): 1782, 1730 cm$^{-1}$

N.M.R. (CDCl$_3$, δ): 1.33 (6H, t, J=7 Hz), 2.33 (2H, d, t, J=20, 8 Hz), 3.8–4.7 (6H, m), 7.8 (4H, s)

(2) Preparation of Diethyl(2-aminooxyethyl)phosphonate

A mixture of diethyl(2-phthalimidoxyethyl)phosphonate (20 g.) and hydrazine.hydrate (3.06 g.) in ethanol (200 ml.) was refluxed under heating for 2 hours with stirring. After cooling, the reaction mixture was filtered to separate insoluble materials, which were washed with chloroform. The combined filtrate and washing was evaporated and to the residue was added chloroform. The mixture was filtered to remove insoluble substances and the filtrate was evaporated. The residue was dissolved in chloroform, treated with activated charcoal and evaporated to give the oily title compound (12.1 g.).

I.R. (Film): 3500, 3350, 3280, 3200 cm$^{-1}$

N.M.R. (CDCl$_3$, δ): 1.28 (6H, t, J=7 Hz), 2.10 (2H, d, t, J=19, 7 Hz), 3.6–4.4 (6H, m), 5.45 (2H, broad s)

(3) Preparation of 2-[2-(O,O-Diethylphosphono)ethoxyimino]-2-(2-formamidothiazol-4-yl)acetic acid (syn isomer)

A mixture of 2-(2-formamidothiazol-4-yl)glyoxylic acid (6 g.) and diethyl(2-aminooxyethyl)phosphonate (7.09 g.) in ethanol (60 ml.) was stirred for 4 hours at room temperature. The reaction mixture was evaporated to dryness and the residue was dissolved in ethyl acetate. This solution was washed successively with 5% hydrochloric acid and water, dried and then evaporated to give the viscous title compound (11.1 g.).

I.R. (CHCl$_3$): 1745, 1710 cm$^{-1}$
N.M.R. (CDCl$_3$, δ): 1.30 (6H, t, J=7 Hz), 2.0–2.7 (2H, m), 3.8–5.0 (6H, m), 7.40 (1H, s), 8.73 (1H, s)

PREPARATION 4

(1) Preparation of N-(3-Pyridyl)-2-bromoacetamide

To a mixture of 3-aminopyridine (11 g.) and triethylamine (13.0 g.) in dry ethyl acetate (300 ml.) was added a solution of bromoacetyl bromide (26.0 g.) in dry ethyl acetate (26 ml.) over a period of 30 minutes with stirring at 0° to 5° C. and stirring was continued for an additional 2 hours at the same temperature. To the reaction mixture was added a chilled aqueous solution of sodium bicarbonate. After shaking well, the ethyl acetate layer was separated, washed successively with water, an aqueous solution of sodium bicarbonate and water, dried and then concentrated. There was obtained concentrate (200 ml.) containing the title compound. Thus obtained concentrate was used directly in the next step reaction without further purification.

(2) Preparation of N-(3-Pyridyl)-2-(phthalimidoxy)acetamide

To a mixture of N-hydroxyphthalimide (17.2 g.) and triethylamide (10.6 g.) in acetonitrile (200 ml.) was added the concentrate containing N-(3-pyridyl)-2-bromoacetamide obtained in preparation 4-(1) with stirring at room temperature and stirring was continued for an hour at 45° go 50° C. To the reaction mixture was added ethyl acetate and water. After shaking well, the ethyl acetate layer was separated, washed successively with water, an aqueous solution of sodium bicarbonate and water, dried, treated with activated charcoal and then concentrated to a volume of 100 to 150 ml. The concentrate was filtered to give the title compound (10.7 g.). The filtrate was evaporated and the residue was washed with diethyl ether to give the same compound (1.9 g.). Total yield: 12.6 g.

I.R. (Nujol): 1795, 1740, 1695 cm$^{-1}$
N.M.R. (DMSO-d$_6$, δ): 4.86 (2H, s), 7.38 (1H, d,d, J=8, 4 Hz), 7.88 (4H, s), 8.08 (1H, d,d, J=8, 2 Hz), 8.32 (1H, d, J=4 Hz), 8.78 (1H, d, J=2 Hz)

(3) Preparation of N-(3-Pyridyl)-2-(aminooxy)acetamide

A mixture of N-(3-pyridyl)-2-(phthalimidoxy)acetamide (7.8 g.) and hydrazine hydrate (1.3 g.) in ethanol (80 ml.) was refluxed under heating for 1.5 hours with stirring. The reaction mixture was cooled and then insoluble substances were filtered out. The filtrate was evaporated and to the residue were added 5% by hydrochloric acid and water. The resulting mixture was filtered to remove insoluble substances and then the filtrate (pH 1 to 2) was concentrated to a volume of 30 ml. to give the concentrate containing the title compound. Thus obtained concentrate was used directly in the next step reaction.

(4) Preparation of 2-[N-(3-Pyridyl)carbamoylmethoxyimino]-2-(2-formamidothiazol-4-yl)acetic acid (syn isomer)

The concentrate (30 ml.) containing N-(3-pyridyl)-2-(aminooxy)-acetamide which was obtained in Preparation 4-(3) was adjusted to pH 3 to 4 with sodium bicarbonate followed by addition of ethanol (100 ml.) and 2-(2-formamidothioazol-4-yl)-glyoxylic acid (4.0 g.) at 15° to 20° C. The resulting mixture was again adjusted to pH 3 to 4 with sodium bicarbonate and then stirred for 3 hours at 18° to 20° C. The reaction mixture was evaporated and the precipitates were collected by filtration and washed with a mixture of water and ethanol to give crystals (6.6 g.). The crystals were dissolved in a mixture of ethanol (20 ml.), water (80 ml.) and sodium bicarbonate (2.38 g.) and then insoluble substances were filtered out. To the filtrate was added 1N hydrochloric acid (28.5 ml.) so that the pH was adjusted to pH 3 to 4. The precipitates were collected by filtration and dried to give crystals of the title compound (6.3 g.).

I.R. (Nujol): 3180, 3050, 1700, 1600 cm$^{-1}$
N.M.R. (D$_2$O+NaHCO$_3$, δ): 5.00 (2H, s), 7.45 (1H, d,d, J=8, 4 Hz), 7.62 (1H, s), 7.9–8.2 (1H, m), 8.37 (1H, d,d, J=4, 2 Hz), 8.63 (1H, s), 8.77 (1H, d, J=2 Hz)

PREPARATION 5

(1) Preparation of tert-Butyl 2-nitrobenzoate

A mixture of 2-nitrobenzoic acid (25.0 g.) and thionyl chloride (50 ml.) was refluxed for an hour and then evaporated. To the residue was added benzene (125 ml.) followed by removal of benzene. To the residue were added benzene (125 ml.), pyridine (23.7 g.) tert-butyl alcohol (22.2 g.) under ice-cooling and then the resulting solution was refluxed under heating for 2 hours. The reaction mixture was poured into ice water. The benzene layer was separated, washed successively with water, 1N aqueous solution of sodium hydroxide (twice), water 1M aqueous solution of citric acid (twice), water and an aqueous solution of sodium chloride, dried over magnesium sulfate and then treated with activated charcoal. Thus obtained organic layer was chromatographed on silica gel (150 g.) eluting with a mixture of benzene and n-hexane (1:1) to give a yellowish oil of the title compound (23.6 g.)

I.R. (Film): 1737, 1540, 1373, 1310, 1232 cm$^{-1}$
N.M.R. (CDCl$_3$, δ): 1.55 (9H, s), 7.17–8.0 (5H, m)

(2) Preparation of tert-Butyl 2-aminobenzoate

A mixture of tert-butyl 2-nitrobenzoate (2.1 g.) in methanol (200 ml.) was hydrogenated over palladium-carbon (2 g.) with shaking at atmospheric pressure and room temperature for 3.5 hours. The reaction mixture was filtered to remove the catalyst and then evaporated. To the residue were successively added diethyl ether and an aqueous solution of sodium chloride followed by shaking. The organic layer was separated, dried over magnesium sulfate, treated with activated charcoal and then evaporated to give an oil of the title compound (16.13 g.).

I.R. (Film): 3520, 3420, 1690, 1610, 1592, 1303, 1252, 1160 cm$^{-1}$
N.M.R. (CCl$_4$, δ):
1.53 (9H, s), 5.67 (2H, broad s), 7.83–6.30 (4H, m)

(3) Preparation of
N-(2-tert-Butoxycarbonylphenyl)-2-bromoacetamide

To a mixture of tert-butyl 2-aminobenzoate (5.79 g.), triethylamine (3.99 g.) in methylene chloride (100 ml.) was added dropwise bromoacetyl bromide (8.01 g.) over a period of 15 minutes with stirring under ice-cooling at 5° to 10° C. following by stirring for 1.75 hours at the same temperature. The reaction mixture was washed successively with 1M aqueous solution of citric acid (50 ml.×2), water a satirated aqueous solution of sodium bicarbonate (25 ml.×2), water and an aqueous solution of sodium chloride, dried over magnesium, treated with activated charcoal and then evaporated to give an oil of the title compound (9.65 g.).

I.R. (Film): 3280, 1690, 1582, 1530, 1450, 1144 cm$^{-1}$
N.M.R. (CCl$_4$, $\delta$): 1.60 (9H, s), 3.88 (2H, s), 8.75–6.83 (4H, m), 11.75 (1H, broad s)

(4) The following compound was prepared by a procedure similar to that described in Preparation 1-(2) or Preparation 4-(2).

tert-Butyl 2-(2-phthalimidoxy)acetamidobenzoate (crystal), mp. 142° to 144° C.

I.R. (Nujol): 3200, 1792, 1745, 1703, 1685, 1525, 1142 700 cm$^{-1}$
N.M.R. (DMSO-d$_6$, $\delta$): 1.58 (9H, s), 4.93 (2H, s), 8.5–7.1 (8H, m), 11.40 (1H, broad s)

(5) The following compound was prepared by a procedure similar to that described in Preparation 1-(3), 2-(2), 3-(2) or 4-(3).

tert-Butyl 2-(2-aminooxyacetamido)benzoate, pm. 87° to 89° C.

I.R. (Nujol): 3300, 1700, 1683, 1592, 1522, 1283, 1162, 1143 cm$^{-1}$
N.M.R. (CDCl$_3$, $\delta$): 7.8–7.0 (4H, m), 6.06 (2H, broad s), 4.28 (2H, s), 1.62 (9H, s)

(6) The following compound was prepared by a procedure similar to that described in Preparation 1-(4), 2-(3), 3-(3) or 4-(4).

2-[N-(2-tert-Butoxycarbonylphenyl)carbamoylmethoxyimino]-2-(2-formamidothiazol-4-yl)acetic acid (syn isomer), mp. 159°–161° C. (dec.).

I.R. (Nujol): 3200, 1745, 1700, 1675, 1598, 1550, 1270 cm$^{-1}$
N.M.R. (DMSO-d$_6$, $\delta$): 1.43 (9H, s), 4.82 (2H, s), 8.70–7.03 (5H, m), 11.43 (1H, s), 12.68 (1H, broad s)

PREPARATION 6

(1) The following compound was prepared by a procedure similar to that described in Preparation 1-(2) or 4-(2).

N-(3-Chlorophenyl)-2-(phthalimidoxy)acetamide.
I.R. (Nujol): 3370, 1795, 1745, 1675 cm$^{-1}$
N.M.R. (DMSO-d$_6$, $\delta$): 4.87 (2H, s), 7.0–7.8 (4H, m), 7.93 (4H, s)

(2) The following compound was prepared by a procedure similar to that described in Preparation 1-(3), 2-(3), 3-(2) or 4-(3).

N-(3-Chlorophenul)-2-(aminooxy)acetamide, mp. 68°–73° C.

I.R. (Nujol): 3350, 3280, 1670, 1595 cm$^{-1}$
N.M.R. (DMSO-d$_6$+D$_2$O, $\delta$): 4.17 (2H, s), 7.0–8.0 (4H, m)

(3) The following compound was prepared by a procedure similar to that described in Preparation 1-(4), 2-(2), 3-(3) or 4-(4).

2-[N-(3-Chlorophenyl)carbamoylmethoxyimino]-2-(2-formamidothiazol-4-yl)acetic acid (syn isomer).
I.R. (Nujol): 3300, 3150, 3050, 1725, 1685, 1620 cm$^{-1}$
N.M.R. (DMSO-d$_6$+D$_2$O, $\delta$): 4.80 (2H, s), 7.0–8.0 (4H, m), 7.63 (1H, s), 8.57 (1H, s)

PREPARATION 7

(1) The following compound was prepared by a procedure similar to that described in Preparation 1-(2) or 4-(2).

N-(2-Thiazolyl)-2-(phthalimidoxy)acetamide.
I.R. (Nujol): 1795, 1745, 1710 cm$^{-1}$
N.M.R. (DMSO-d$_6$, $\delta$): 4.92 (2H, s), 7.26 (1H, d, J=4 Hz), 7.50 (1H, d, J=4 Hz), 7.86 (4H, s)

(2) The following compound was prepared by a procedure similar to that described in Preparation 1-(3), 2-(2), 3-(2) or 4-(3).

N-(2-Thiazonyl)-2-(aminooxy)acetamide
I.R. (Nujol): 3350, 3300, 3200, 1700, 1580 cm$^{-1}$
N.M.R. (DMSO-d$_6$+D$_2$O, $\delta$): 4.34 (2H, s), 7.22 (1H, d, J=4 Hz), 7.50 (1H, d, J=4 Hz)

(3) The following compound was prepared by a procedure similar to that described in Preparation 1-(4), 2-(3), 3-(3) or 4-(4).

2-[N-(2-Thiazolyl)carbamoylmethoxyimino]-2-(2-formimidothiazol-4-yl)acetic acid (syn isomer).
I.R. (Nujol): 1700, 1670, 1580, 1560 cm$^{-1}$
N.M.R. (DMSO-d$_6$+D$_2$O, $\delta$): 4.94 (2H, s), 7.26 (1H, d, J=4 Hz), 7.50 (1H, d, J=4 Hz), 7.60 (1H, s), 8.56 (1H, s)

PREPARATION 8

The following compound was prepared by a procedure similar to that described in Preparation 1-(4), 2-(3), 3-(3) or 4-(4).

2-[N-(2-Hydroxy-3,5-dichlorophenyl)carbamoylmethoxyimino]-2-(2-formamidothiazol-4-yl)acetic acid (syn isomer).
I.R. (Nujol): 3330, 1755, 1720, 1680, 1590, 1540 cm$^{-1}$
N.M.R. (DMSO-d$_6$+D$_2$O, $\delta$): 4.93 (2H, s), 7.28 (1H, d, J=3 Hz), 7.67 (1H, s), 8.00 (1H, d, J=3 Hz), 8.60 (1H, s)

PREPARATION 9

(1) Preparation of
2-(2-aminoethoxyimino)-2-(2-formamidothiazol-4-yl)acetic acid (syn isomer)

To a solution of 2-(2-formamidothiazol-4-yl)glyoxylic acid (5.5 g.) in ethanol (100 ml.) was added a solution of 2-(aminooxy)ethylamine.dihydrochloride (4.1 g.) in water (50 ml). The resulting mixture was adjusted to pH 4 with an aqueous solution of sodium bicarbonate and stirred for 3 hours at room temperature. The reaction mixture was evaporated to a volume of 100 ml. and cooled. The resulting precipitates were collected by filtration, washed successively with cold-water and ethanol to give the title compound (6.5 g.), mp 213° to 214° C. (dec.).

I.R. (Nujol): 3500–2100, 1705, 1658, 1590 cm$^{-1}$
N.M.R. (DMSO-d$_6$, $\delta$): 8.58 (1H, s), 7.42 (1H, s), 4.5–3.92 (2H, m), 3.25–2.67 (2H, m)

(2) Preparation of
2-[2-(2-Hydroxy-5-chlorobenzamido)ethoxyimino]-2-(2-formamidothiazol-4-yl)acetic acid (syn isomer)

To a suspension of 2-(2-aminoethoxyimino)-2-(2-formamido)thiazol-4-yl)acetic acid (syn isomer) (5.10 g.) in methylene chloride (100 ml.) was added 1,5-diazabicyclo[5,4,0]undecene-5 (7.2 g.) to give a solution and thereto was added trimethylsilylchloride (5.14 g.) followed by stirring for an hour at 10° C. After bistrimethylsilyl)acetamide (21.7 g.) was added, the mixture was stirred for 5 minutes at 10° C. To thus obtained homogeneous solution was added a solution of 2-hydroxy-5-chlorobenzoyl chloride (4.54 g.) in methylene chloride (20 ml.) at −15° to −5° C. followed by stirring for 2 hours at −5° to 5° C. and for an hour at room temperature. The reaction mixture was concentrated to dryness and to the residue was added cold water and ethyl acetate. After the mixture was adjusted to pH 8 with sodium bicarbonate, the aqueous layer was separated, washed with ethyl acetate, then adjusted to pH 2 with 10% hydrochloric acid, and extracted with ethyl acetate. The extract was washed with water, dried over magnesium sulfate and then concentrated to dryness. The residue was triturated with diethyl ether to give the title compound (4.1 g.).

I.R. (Nujol): 3400, 3220, 3090, 1745, 1681, 1642, 1600, 1557 cm$^{-1}$

N.M.R. (DMSO-d$_6$+D$_2$O, δ): 8.60 (1H, s), 7.97 (1H, d, J=2 Hz), 7.60 (1H, s), 7.46 (1H, d,d, J=2, 9 Hz), 7.00 (1H, d, J=9 Hz), 4.35 (2H, t, J=6 Hz), 3.72 (2H, t, J=6 Hz)

PREPARATION 10

(1) A mixture of 2-(2-formamidothiazol-4-yl)-glyoxylic acid (1.59 g.), tert-butyl N-aminooxyethylcarbamate (1.40 g.) and methanol (25 ml.) was stirred at room temperature for 6 hours. After removal of methanol from the resultant solution under reduced pressure, the residue was pulverized with diethyl ether. The precipitates were collected by filtration to give 2-[2-(tert-butoxycarboxamido)ethoxyimino]-2-(2-formamidothiazol-4-yl)acetic acid (syn isomer) (2.20 g.).

I.R. $v_{max}^{Nujol}$: 3140, 1698, 1604 cm$^{-1}$

N.M.R. δ(DMSO-d$_6$, ppm): 1.37 (9H, s), 3.20 (2H, m), 3.97 (2H, m), 6.73 (1H, broad s), 7.33 (1H, s), 8.50 (1H, s)

(2) Vilsmeier reagent was prepared from N,N-dimethylformamide (0.98 g.) and phosphoryl chloride (2.05 g.) in ethyl acetate (6 ml.) in a usual manner. 2-[2-(tert-Butoxycarboxamido)ethyoxyimino]-2-(2-formamidothiazol-4-yl)acetic acid (syn isomer) (4.0 g.) was added to the stirred suspension of the Vilsmeier reagent in ethyl acetate (26 ml.) under ice cooling. The resulting mixture was added to a solution of 7-amino-3-(1,3,4-thiadiazol-2-yl)-thiomethyl-3-cephem-4-carboxylic acid (3.7 g.) and trimethylsilylacetamide (8.7 g.) in tetrahydrofuran (37 ml.) at −25° C. and the mixture was stirred for 30 minutes at −15° C. After addition of water (100 ml.) and tetrahydrofuran (40 ml.) to the reaction mixture, the organic layer was separated. To the organic layer was added water (100 ml.) and then the mixture was adjusted to pH 7.5 with sodium bicarbonate. The aqueous layer was separated and thereto was added tetrahydrofuran. The mixture was adjusted to pH 3.0 with 10% hydrochlonic acid. The organic layer was separated, washed with a saturated aqueous solution of sodium chloride, dried over magnesium sulfate and evaporated under reduced pressure to give 7-[2-[2-(tert-butoxycarboxamido)ethoxyimino]-2-(2-formamidothiazol-4-yl)acetamide]-3-(1,3,4-thiadiazol-2-yl)-thiomethyl-3-cephem-4-carboxylic acid (syn isomer) (5.9 g.).

I.R. ν(Nujol) 3400–3100, 1780, 1680, 1540 cm$^{-1}$

N.M.R. (DMSO-d$_6$, δ, ppm): 1.35 (9H, s), 2.95–3.53 (2H, m), 3.53–3.90 (2H, m), 3.90–4.28 (2H, m) 4.45 (2H, q, J=14 Hz), 5.17 (1H, d, J=5 Hz), 5.85 (1H, dd, J=5 and 8 Hz), 7.4 (1H, s), 8.52 (1H, s), 9.53 (1H, s), 9.57 (1H, d, J=8 Hz), 12.6 (1H, broad s)

(3) A mixture of 7-[2-[2-(tert-butoxycarboxamido)ethoxyimino]-2-(2-formamidothiazol-4-yl)acetamido]-3-(1,3,4-thiadiazol-2-yl)thiomethyl-3-cephem-4-carboxylic acid (syn isomer) (5.8 g.) and formic acid (60 ml.) was stirred for 3 hours at 40° C. The reaction mixture was evaporated under reduced pressure. The residue was pulverized in acetonitrile and then washed with diethyl ether to give 7-[2-(2-aminoethoxyimino)-2-(2-formamidothiazol-4-yl)acetamido]-3-(1,3,4-thiadiazol-2-yl)thiomethyl-3-cephem-4-carboxylic acid formate (syn isomer) (4.4 g.).

N.M.R. (DMSO-d$_6$, δ, ppm): 3.23 (2H, m), 4.07–4.77 (4H, m), 5.08 (1H, d, J=5 Hz), 5.78 (1H, dd, J=5 and 8 Hz), 7.52 (1H, s), 8.53 (1H, s), 9.5 (1H, s), 9.55 (1H, d, J=8 Hz), 3.52 (2H, m)

Preparation of the object compound

EXAMPLE 1

Preparation of 7-[2-{N-(2-Hydroxy-5-chlorophenyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer)

A mixture of N,N-dimethylformamide (10 ml.) and phosphorus oxychloride (0.507 g.) was warmed at 40° C. for 30 minutes and subsequently cooled to −10° C. and thereto was added 2-[N-(2-hydroxy-5-chlorophenyl)carbamoylmethoxyimino]-2-(2-formamidothiazol-4-yl)acetic acid (syn isomer) (1.00 g.). The resulting mixture was stirred at −10° to −5° C. for 50 minutes. On the other hand, to a solution of trimethylsilylacetamide (3.60 g.) in methylene chloride (15 ml.) was added 7-amino-3-(1-methyl-1H-tetrazol-5-yl)thiomethyl-3-cephem-4-carboxylic acid (1.003 g.). To this solution was added the stirred mixture obtained above at −25° C. followed by stirring at −20° to −10° C. for 2 hours. After concentration of the reaction mixture, to the residue were added a saturated aqueous solution of sodium bicarbonate (25 ml.) and water (50 ml.). The resulting mixture was washed with ethyl acetate and thereto was added ethyl acetate (100 ml.). The mixture was adjusted to pH 2 with 10% hydrochloric acid and extracted with ethyl acetate. The extract was washed with water, dried over magnesium sulfate, treated with activated charcoal and then concentrated. The residue was triturated with diethyl ether and the precipitates were collected by filtration and then washed with diethyl ether to give a powder (1.0 g.), which was dissolved in a small amount of a mixture of acetone and ethyl acetate. This solution was washed with water twice, dried over magnesium sulfate and then concentrate to a small volume. To the concentrate was added diethyl ether followed by stirring at room temperature overnight. The precipitates were collected by filtration, washed with diethyl ether and dried to give the title compound (0.63 g.).

I.R. (Nujol): 3250, 1780, 1680 cm$^{-1}$

N.M.R. (DMSO-d$_6$+D$_2$O, δ): 3.7 (2H, broad s), 3.92 (3H, s), 4.3 (2H, broad s), 4.8 (2H, broad s), 5.18 (1H, d, J=5 Hz), 5.87 (1H, d, J=5 Hz), 6.8–7.2 (2H, m), 7.57 (1H, s), 7.97 (1H, d, J=2 Hz), 8.53 (1H, s)

EXAMPLE 2

Preparation of 7-[2-(O,O-Diethylphosphono)methoxyimino-2-(2-formamidothiazol-4-yl)acetamido]-3-(1-methyl-1H-tetrazol-5-yl)thiomethyl-3-cephem-4-carboxylic acid (syn isomer)

A mixture of N,N-dimethylformamide (1.09 g.) and phosphorus oxychloride (2.08 g.) was warmed for 30 minutes at 40° C. Dry methylene chloride (30 ml.) was added thereto at −15° C. and then a mixture of 2-(O,O-diethylphosphono)methoxyimino-2-(2-formamidothiazol-4-yl)acetic acid (syn isomer) (4.5 g.) and dry methylene chloride (40 ml.) was added thereto at −10° C. The resulting mixture was stirred for an hour at −5° to −10° C. On the other hand, a mixture of 7-amino-3-(1-methyl-1H-tetrazol-5-yl)-thiomethyl-3-cephem-4-carboxylic acid (4.9 g.), trimethylsilylacetamide (10.6 g.) and dry methylene chloride (75 ml.) was stirred for 15 minutes at 35° to 40° C. to give a clear solution. To this solution was added at −15° to −10° C. the above-obtained methylene chloride solution, and the resulting mixture was stirred for an hour at −5° to −10° C. and then for an hour at 5° C. The reaction mixture was evaporated, and cold water and sodium bicarbonate were added to the residue. The solution was washed with ethyl acetate. The aqueous layer was adjusted to pH 3 to 4 with 10% hydrochloric acid after addition of ethyl acetate. The mixture was shaken and the ethyl acetate layer was separated. The aqueous layer was further adjusted to pH 3 to 4 with 10% hydrochloric acid after addition of ethyl acetate and shaker. The ethyl acetate layer was combined with the ethyl acetate layer separated before. The combined ethyl acetate solution was washed with water, dried and evaporated. To the residue was added diethyl ether to give a powder which was washed with a small amount of ethyl acetate to give a power of the title compound (4.6 g.).

I.R. (Nujol): 3200, 1790, 1730, 1690 cm$^{-1}$

N.M.R. (DMSO-$d_6$, δ): 1.2 (6H, t, J=7 Hz), 3.67 (2H, broad s), 3.7–4.7 (8H, s), 3.90 (3H, s), 5.13 (1H, d, J=5 Hz), 5.78 (1H, d, d, J=8, 5 Hz), 7.43 (1H, s), 8.50 (1H, s)

EXAMPLE 3

Preparation of 7-[2-{2-(O,O-Diethylphosphono)ethoxyimino}-2-(2-formamidothiazol-4-yl)acetamido]-3-(1-methyl-1H-tetrazol-5-yl)thiomethyl-3-cephem-4-carboxylic acid (syn isomer)

A mixture of phosphorus oxychloride (4.9 g.) and N,N-dimethylformamide (2.56 g.) was warmed for 30 minutes at 40° C. and thereto was added dry methylene chloride (50 ml). To the mixture was added a mixture of 2-[2-(O,O-diethylphosphono)ethoxyimino]-2-(2-formamidothiazol-4-yl)-acetic acid (syn isomer) (9.3 g.) in dry methylene chloride (50 ml.) over a period of 5 minutes with stirring at −5° to −10° C. and stirring was continued for 40 minutes at −10° C. On the other hand, a mixture of 7-amino-3-(1-methyl-1H-tetrazol-5-yl)thiomethyl-3-cephem-4-carboxylic acid (10.72 g.) and trimethylsilylacetamide (31 g.) in methylene chloride (150 ml.) was stirred for 15 minutes at 35° to 40° C. and then cooled to −15° C. To the mixture was added the stirred solution obtained above at −15° C. followed by stirring for an hour at −10° to −5° C. and for an additional 30 minutes at −5° to 0° C. After concentration of the reaction mixture, to the residue were added ethyl acetate (500 ml.) and ice-cold water (200 ml.). The resulting mixture was shaken and the ethyl acetate layer was separated, washed with water, dried and then concentrated. To the residue (15 g.) was added ethyl acetate followed by stirring overnight. The precipitates were collected by filtration to give a powder, to which was added a small amount of ethyl acetate followed by stirring. The precipitate was again collected by filtration and dried to give a powder of the title compound (9.7 g.).

I.R. (Nujol): 1785, 1730, 1690 cm$^{-1}$

N.M.R. (DMSO-$d_6$+$D_2O$, δ): 1.24 (6H, t, J=7 Hz), 2.0–2.6 (2H, m), 3.4–4.6 (10H, m), 3.96 (3H, s), 5.20 (1H, d, J=5 Hz), 5.85 (1H, d, J=5 Hz), 7.50 (1H, s), 8.54 (1H, s)

EXAMPLE 4

Preparation of 7-[2-{2-(O,O-Diethylphosphono)ethoxyimino}-2-(2-formamidothiazol-4-yl)acetamido]-3-(2-benzothiazolyl)thiomethyl-3-cephem-4-carboxylic acid (syn isomer)

A mixture of phosphorus oxychloride (1.397 g.) and N,N-dimethylformamide (0.73 g.) was added to methylene chloride (1 ml.) at below 40° C. followed by stirring for 30 minutes at 40° C. After addition of methylene chloride (20 ml.) and cooling to −11° C., to the mixture was added a mixture of 2-[2-(O,O-diethylphosphono)ethoxyimino]-2-(2-formamidothiazol-4-yl)acetic acid (syn isomer) (2.65 g.) in methylene chloride (20 ml.) over a period of 5 minutes with stirring at −11° to −8° C. and then stirring was continued for 40 minutes at −10° to −8° C. On the other hand, a mixture of 7-amino-3-(2-benzothiazolyl)thiomethyl-3-cephem-4-carboxylic acid (2.65 g.) and trimethylsilylacetamide (10.1 g) was dissolved in methylene chloride (50 ml.). To this solution was at a time added the stirred mixture obtained above under cooling at −30° C. followed by stirring 1.5 hours at −10° to −8° C. After removal of the solvent from the reaction mixture, to the residue were added ethyl acetate and water. The ethyl acetate layer was washed with a diluted hydrochloric acid (pH about 2) and then extracted with a saturated aqueous solution of sodium bicarbonate. The extract was washed with ethyl acetate and thereto was added ethyl acetate. After the mixture was adjusted to pH about 2 with 10% hydrochloric acid, the ethyl acetate layer was separated, washed successively with water and an aqueous layer of sodium chloride, dried over magnesium sulfate, treated with activated charcoal and then evaporated. The residue was triturated with diethyl ether and the precipitates were collected by filtration and then dried to give the title compound (3.37 g.), mp. 132° to 150° C. (dec.)

I.R. (Nujol): 3200, 1790, 1690 cm$^{-1}$

N.M.R. (DMSO-$d_6$, δ): 1.20 (6H, t, J=7 Hz), 2.0–2.6 (2H, m), 3.60, 3.88 (2H, ABq, J=18 Hz), 3.9–5.0 (8H, m), 5.20 (1H, d, J=5 Hz), 5.85 (1H, d,d, J=5, 8 Hz), 7.50 (1H, s), 7.2–8.1 (4H, m), 8.52 (1H, s), 9.70 (1H, d, J=8 Hz)

EXAMPLE 5

Preparation of
7-[2-{N-(3-Pyridyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer)

A mixture of phosphorus oxychloride (1.6 g.) and N,N-dimethylformamide (31 ml.) was warmed at 40° C. for 30 minutes followed by cooling to −10° C. To the mixture was added 2-[N-(3-pyridyl)carbamoylmethoxyimino]-2-(2-formamidothiazol-4-yl)acetic acid (syn isomer) (3.1 g.) followed by stirring for an hour at −10° to −7° C. On the other hand, a mixture of 7-amino-3-(1-methyl-1H-tetrazol-5-yl)thiomethyl-3-cephem-4-carboxylic acid (3.2 g.) and trimethylsilylacetamide (7 g.) in methylene chloride (60 ml.) was stirred for 30 minutes at room temperature and then cooled to −15° C. To the mixture was added the above obtained dimethylformamide mixture followed by stirring for 1.5 hours at −15° to −10° C. To the reaction mixture were added ice-cold water and sodium bicarbonate. The aqueous layer (pH 7 to 8) was separated and washed with ethyl acetate and then thereto was added ethyl acetate. After the pH was adjusted to 3 to 4 with 10% hydrochloric acid, the precipitates were collected and then dissolved in an aqueous solution of sodium bicarbonate. The resulting mixture was treated with activated charcoal and the aqueous layer was separated and then adjusted to pH 3 to 4 with 10% hydrochloric acid. The precipitates were collected by filtration and dried to give the title compound (2.0 g.).

I.R. (Nujol): 1780, 1680 cm$^{-1}$

N.M.R. (DMSO-d$_6$+D$_2$O, δ): 3.7 (2H, broad s), 3.90 (3H, s), 4.30 (2H, broad s), 4.8 (2H, broad s), 5.20 (1H, d, J=4.5 Hz), 5.90 (1H, d, J=4.5 Hz), 7.2–7.5 (1H, m), 7.57 (1H, s), 7.9–8.4 (2H, m), 8.53 (1H, s), 8.8 (1H, broad s)

EXAMPLE 6

The following compounds were prepared by procedures similar to those described in Examples 1 to 5.

(1) 7-[2-{N-(2-tert-Butoxycarbonylphenyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer), mp. 175° to 185° C. (dec.)

I.R. (Nujol): 3500–3100, 1790, 1700, 1540 cm$^{-1}$

N.M.R. (DMSO-d$_6$, δ): 9.38 (1H, broad d, J=9 Hz), 8.58 (1H, s), 8.6–7.1 (5H, m), 6.00 (1H, d, d, J=5, 9 Hz), 5.25 (1H, d, J=5 Hz), 4.83 (2H, s), 4.35 (2H, broad s), 3.97 (3H, s), 3.73 (2H, broad s), 1.47 (9H, s)

(2) 7-[2-{N-(3-Chlorophenyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer)

I.R. (Nujol): 3300, 1785, 1690 cm$^{-1}$

N.M.R. (DMSO-d$_6$, δ): 3.7 (2H, broad s), 3.93 (3H, s), 4.3 (2H, broad s), 4.8 (2H, broad s), 5.20 (1H, d, J=4.5 Hz), 5.92 (1H, d, d, J=4.5, 8 Hz), 7.0–8.0 (4H, m), 7.57 (1H, s), 8.53 (1H, s)

(3) 7-[2-{N-(2-Thiazolyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer)

I.R. (Nujol): 3250, 1785, 1740, 1700, 1670 cm$^{-1}$

N.M.R. (DMSO-d$_6$, δ): 3.7 (2H, broad s), 3.93 (3H, s), 4.3 (2H, broad s), 4.9 (2H, broad s), 5.20 (1H, d, J=5 Hz), 5.90 (1H, d, d, J=5, 8 Hz), 7.25 (1H, d, J=4 Hz), 7.50 (1H, d, J=4 Hz), 7.53 (1H, s), 8.53 (1H, s), 9.90 (1H, d, J=8 Hz)

(4) 7-[2-{N-(2-Hydroxy-3,5-dichlorophenyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer)

(5) 7-[2-{2-(2-Hydroxy-5-chlorobenzamido)ethoxyimino}-2-(2-formamidothiazol-4-yl)acetamido]-3-(1-methyl-1H-tetrazol-5-yl)thiomethyl-3-cephem-4-carboxylic acid (syn isomer), powder.

I.R. (Nujol): 3220, 1797, 1697, 1650, 1595, 1535, 1470 cm$^{-1}$

N.M.R. (DMSO-d$_6$+D$_2$O, δ): 8.53 (1H, s), 7.87 (1H, d, J=2 Hz), 7.47 (1H, s), 7.38 (1H, d, d, J=2, 9 Hz), 6.90 (1H, d, J=9 Hz), 5.85 (1H, d, J=5 Hz), 5.12 (1H, d, J=5 Hz), 4.5–4.0 (4H, m), 3.92 (3H, s), 3.8–3.1 (4H, m)

(6) 7-[2-{N-(2-Hydroxy-5-chlorophenyl)carbamoylmethoxyimino}-2-(2-formamidothiazol-4-yl)acetamido}-cephalosporanic acid (syn isomer), mp. 170° to 190° C. (dec. with changing color).

I.R. (Nujol): 3250, 1785, 1740, 1670 cm$^{-1}$

N.M.R. (DMSO-d$_6$+D$_2$O, δ): 2.02 (3H, s), 3.46, 3.65 (2H, ABq, J=17 Hz), 4.77, 5.02 (2H, ABq, J=13 Hz), 4.85 (2H, s), 5.22 (1H, d, J=5 Hz), 5.91 (1H, d, J=5 Hz), 6.85–7.15 (2H, m), 7.57 (1H, s), 8.00 (1H, d, J=2 Hz), 8.54 (1H, s)

(7) 7-[2-{N-(3-Chlorophenyl)carbamoylmethoxyimino}-2-(2-formamidothiazol-4-yl)acetamido]-3-(5-methyl-1,3,4-thiadiazol-2-yl)thiomethyl-3-cephem-4-carboxylic acid (syn isomer), mp. 160° C. (dec.).

I.R. (Nujol): 3300, 1785, 1680 cm$^{-1}$

N.M.R. (DMSO-d$_6$+D$_2$O, δ): 2.72 (3H, s), 3.75 (2H, broad s), 4.30, 4.57 (2H, ABq, J=14 Hz), 4.83 (2H, broad s), 5.27 (1H, d, J=5 Hz), 6.00 (1H, d, J=5 Hz), 7.0–8.0 (5H, m), 8.58 (1H, s)

(8) 7-[2-{N-(2-Hydroxy-5-chlorophenyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp. 165° to 175° C. (dec.).

(9) 7-[2-Phosphonomethoxyimino-2-(2-aminothiazol-4-yl)acetamido]-3-(1-methyl-1H-tetrazol-5-yl)thiomethyl-3-cephem-4-carboxylic acid (syn isomer), mp. 210° to 220° C. (dec.).

(10) 7-[2-{2-(O,O-Diethylphosphono)ethoxyimino}-2-(2-aminothiazol-4-yl)acetamido]-3-(1-methyl-1H-tetrazol-5-yl)thiomethyl-3-cephem-4-carboxylic acid.hydrochloride (syn isomer), mp. 170° to 180° C. (dec.).

(11) 7-[2-(2-Phosphonoethoxyimino)-2-(2-aminothiazol-4-yl)acetamido]-3-(1-methyl-1H-tetrazol-5-yl)-thiomethyl-3-cephem-4-carboxylic acid (syn isomer), mp. 180° to 210° C. (dec.).

(12) 7-[2-(2-Phosphonoethoxyimino)-2-(2-aminothiazol-4-yl)acetamido]-3-(2-benzothiazolyl)thiomethyl-3-cephem-4-carboxylic acid (syn isomer), mp. 170° to 210° C. (dec.).

(13) 7-[2-{N-(3-Pyridyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), powder, mp. 180° to 210° C. (dec.).

(14) 7-[2-{N-(2-Carboxyphenyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp. 220° to 230° C. (dec.).

(15) 7-[2-{N-(3-Chlorophenyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp. 191° to 195° C. (dec.).

(16) 7-[2-{N-(2-Thiazolyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp. 180° to 185° C. (dec.)

(17) 7-[2-{N-(2-Hydroxy-3,5-dichlorophenyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp. 161° to 170° C. (dec.).

(18) 7-[2-{2-(2-Hydroxy-5-chlorobenzamido)ethoxyimino}-2-(2-aminothiazol-4-yl)acetamido]-3-(1-methyl-1H-tetrazol-5-yl)thiomethyl-3-cephem-4-carboxylic acid (syn isomer), mp. 220° to 230° C. (dec.).

(19) 7-[2-{N-(2-Hydroxy-5-chlorophenyl)carbamoylmethoxyimino}-2-(2-aminothiazol-4-yl)acetamido]-cephalosporanic acid (syn isomer), mp. >250° C.

(20) 7-[2-{N-(3-Chlorophenyl)carbamoylmethoxyimino}-2-(2-aminothiazol-4-yl)acetamido]-3-(5-methyl-1,3,4-thiadiazol-2-yl)thiomethyl-3-cephem-4-carboxylic acid (syn isomer), mp. 173° C. (dec.).

(21) 7-[2-[2-[{3-(2-Chlorophenyl)-5-methylisoxazol-4-yl}carboxamino]ethoxyimino]-2-(2-formamidothiazol-4-yl)acetamido]-3-(1,3,4-thiadiazol-2-yl)thiomethyl-3-cephem-4-carboxylic acid (syn isomer).

I.R. (Nujol): 3400–3100, 1780, 1660, 1540 cm$^{-1}$

(22) 7-[2-[2-[{3-(2-Chlorophenyl)-5-methylisoxazol-4-yl}carboxamido]ethoxyimino]-2-(2-aminothiazol-4-yl)acetamido]-3-(1,3,4-thiadiazol-2-yl)thiomethyl-3-cephem-4-carboxylic acid (syn isomer).

I.R. (Nujol): 3400–3100, 1770, 1650, 1520 cm$^{-1}$

EXAMPLE 7

Preparation of 7-[2-{N-(2-Hydroxy-5-chlorophenyl)carbamoylmethoxyimino}-2-(2-aminothiazol-4-yl)-acetamido]-3-(1-methyl-1H-tetrazol-5-yl)thiomethyl-3-cephem-4-carboxylic acid (syn isomer)

To a mixture of acetone (1 ml.), methanol (4 ml.) and 7-[2-{N-(2-hydroxy-5-chlorophenyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer) (0.55 g.) was added conc. hydrochloric acid (0.11 ml.) followed by stirring for 3 hours at room temperature. The reaction mixture was concentrated and then to the residue were added water (3 ml.) and an aqueous solution of sodium bicarbonate whereby the pH was adjusted to about 2. The resulting mixture was stirred at room temperature and the precipitates were collected by filtration, washed with water and then dried to give the title compound (0.40 g.), mp. 165° to 175° C. (dec.)

I.R. (Nujol): 3300, 3200, 1780, 1680, 1640, 1610 cm$^{-1}$

N.M.R. (DMSO-d$_6$+D$_2$O, δ): 3.7 (2H, broad s), 3.90 (3H, s), 4.3 (2H, broad s), 4.8 (2H, broad s), 5.14 (1H, d, J=5 Hz), 5.80 (1H, d, J=5 Hz), 6.7–7.1 (3H, m), 8.0 (1H, broad s)

EXAMPLE 8

Preparation of 7-[2-Phosphonomethoxyimino-2-(2-aminothiazol-4-yl)acetamido]-3-(1-methyl-1H-tetrazol-5-yl)-thiomethyl-3-cephem-4-carboxylic acid (syn isomer)

A mixture of 7-[2-(O,O-diethylphosphono)methoxyimino-2-(2-formamidothiazol-4-yl)acetamido]-3-(1-methyl-1H-tetrazol-5-yl)thiomethyl-3-cephem-4-carboxylic acid (syn isomer) (4.3 g.), methylene chloride (65 ml.) and bis(trimethylsilyl)acetamide (6.5 g.) was stirred for 30 minutes at room temperature and thereto was added trimethylsilylbromide (4.85 g.) over a period of 15 minutes with stirring at about 20° C. and then the stirring was continued for an additional 4 hours at room temperature. The reaction mixture containing 7-[2-phosphonomethoxyimino-2-(2-formamidothiazol-4-yl)acetamido]-3-(1-methyl-1H-tetrazol-5-yl)thiomethyl-3-cephem-4-carboxylic acid (syn isomer) was concentrated and then to the residue was added methanol (65 ml.) under cooling followed by addition of conc. hydrochloric acid (2 ml.) with stirring. The resulting mixture was stirred for 1.5 hours at room temperature and concentrated. To the residue was added water (150 ml.) and the mixture was washed with ethyl acetate twice. The aqueous layer was adjusted to pH 2 to 3, with sodium bicarbonate and subjected to column chromatography (non-ion adsorption resin, Diaion HP20 prepared by Mitsubishi Chemical Industries) (150 ml.) and the column was washed with water and then eluted successively with 10% methanol (1 l.), 20% methanol (1 l.) and 30% methanol (3 l.). The fractions containing the desired compound were evaporated to give the title compound (2.6 g.) mp. 210° to 220° C. (dec.)

I.R. (Nujol): 1770, 1650 cm$^{-1}$

N.M.R. (DMSO-d$_6$+D$_2$O, δ) 3.7 (2H, broad s), 3.94 (3H, s), 4.3 (4H, broad s), 5.14 (1H, d, J=5 Hz), 5.76 (1H, d, J=5 Hz), 6.80 (1H, s)

EXAMPLE 9

Preparation of 7-[2-{2-(O,O-Diethylphosphono)ethoxyimino}-2-(2-aminothiazol-4-yl)acetamido]-3-(1-methyl-1H-tetrazol-5-yl)thiomethyl-3-cephem-4-carboxylic acid hydrochloride (syn isomer)

To a mixture of 7-[2-{2-(O,O-diethylphosphono)ethoxyimino}-2-(2-formamidothiazol-4-yl)acetamido]-3-(1-methyl-1H-tetrazol-5-yl)thiomethyl-3-cephem-4-carboxylic acid (syn isomer) (0.9 g.) and methanol (10 ml.) was added conc. hydrochloric acid (0.2 ml.) followed by stirring for 2.5 hours at room temperature. The reaction mixture was concentrated and to the residue was added ethyl acetate followed by stirring. The precipitates were collected by filtration to give the title compound (0.85 g.), mp. 170° to 180° C. (dec.).

I.R. (Nujol): 1780, 1720, 1680, 1630 cm$^{-1}$

N.M.R. (DMSO-d$_6$, δ): 1.23 (6H, t, J=7 Hz), 1.9–2.5 (2H, m), 4.00 (3H, s), 3.5–4.8 (10H, m), 5.23 (1H, d, J=4.5 Hz), 5.83 (1H, d, d, J=4.5, 8 Hz), 7.10 (1H, s), 9.93 (1H, d, J=8 Hz)

EXAMPLE 10

Preparation of 7-[2-(2-Phosphonoethoxyimino)-2-(2-aminothiazol-4-yl)acetamido]-3-(1-methyl-1H-tetrazol-5-yl)thiomethyl-3-cephem-4-carboxylic acid (syn isomer)

A mixture of 7-[2-{2-(O,O-diethylphosphono)ethoxyimino}-2-(2-formamidothiazol-4-yl)acetamido]-3-(1-methyl-1H-tetrazol-5-yl)thiomethyl-3-cephem-4-carboxylic acid (syn isomer) (6.2 g.) methylene chloride (90 ml.) and bis(trimethylsilyl)acetamide (9.2 g.) was stirred for 30 minutes at room temperature and thereto was added trimethylsilyl bromide (6.9 g.) over a period of 30 minutes with stirring at 20° to 25° C. and then stirring was continued for 5 hours at 25° to 27° C. The reaction mixture containing 7-[2-(2-phosphonoethoxyimino)-2-(2-formamidothiazol-4-yl)acetamido]-3-(1-methyl-1H-tetrazol-5-yl)thiomethyl-3-cephem-4-carboxylic acid (syn isomer) was concentrated and to the residue were added cold methanol (100 ml.) and cold conc. hydrochloric acid (4 ml.) followed by stirring for an hour at room temperature and a further addition of conc. hydrochloric acid (2 ml.). The resulting mixture was stirred for an hour at room temperature and then concentrated. To the residue was added water (300 ml.) and the mixture was adjusted to pH 2 to 3 with sodium bicarbonate and then subjected to column chromatography (non-ion adsorption resin, Diaion HP 20 prepared by Mitsubishi Chemical Industries) (200 ml.). The column was washed with water (1 l.) and then eluted successively with 10% methanol (1 l.), 20% methanol (1 l.), 30% methanol (1 l.) and 40% methanol (2 l.). The fractions containing the desired compound were evaporated to give the title compound (3.7 g.), mp. 180° to 210° C. (dec.)

I.R. (Nujol): 3300, 1780, 1670, 1640 cm$^{-1}$

N.M.R. (DMSO-$d_6$+$D_2O$, δ): 1.7–2.4 (2H, m), 3.7 (2H, broad s), 3.92 (3H, s), 4.0–4.6 (4H, m), 5.10 (1H, d, J=5 Hz), 5.77 (1H, d, J=5 Hz), 6.77 (1H, s)

EXAMPLE 11

Preparation of 7-[2-(2-Phosphonoethoxyimino)-2-(2-aminothiazol-4-yl)acetamido]-3-(2-benzothiazolyl)thiomethyl-3-cephem-4-carboxylic acid (syn isomer)

A mixture of 7-[2-{2-(O,O-diethylphosphono)ethoxyimino}-2-(2-formamidothiazol-4-yl)acetamido]-3-(2-benzothiazolyl)thiomethyl-3-cephem-4-carboxylic acid (syn isomer) (2.59 g.), methylene chloride (30 ml.) and bis(trimethylsilyl)acetamide (2.14 g.) was stirred for 30 minutes at 18° to 20° C. and thereto was added trimethylsilyl bromide (2.68 g.) followed by stirring for 5 hours and 45 minutes at 19° to 21° C. The reaction mixture containing 7-[2-(2-phosphonoethoxyimino)-2-(2-formamidothiazol-4-yl)acetamido]-3-(2-benzothiazolyl)thiomethyl-3-cephem-4-carboxylic acid (syn isomer) was concentrated and to the residue were added methanol (30 ml.) and conc. hydrochloric acid (3 ml.). The mixture was stirred for 1.5 hours at room temperature and then evaporated. The residue was dissolved in an aqueous solution of sodium bicarbonate and the solution was washed with ethyl acetate and then adjusted to pH about 2 with 10% hydrochloric acid. The precipitates were collected by filtration under cooling, washing with water, dried under reduced pressure and then suspended in methanol (20 ml.). After conc. hydrochloric acid was added to the suspension to dissolve the precipitates, the resulting solution was treated with activated charcoal and then thereto was added dropwise a mixture of conc. ammonia water and methanol (1:5) whereby the pH was adjusted to 3 to 4. The precipitates were collected by filtration under cooling to give a powder of the title compound (0.85 g.), mp. 170° to 210° C.

I.R. (Nujol): 1780, 1680, 1630 cm$^{-1}$

N.M.R. (73° C., $D_2O$+NaHCO$_3$, δ): 1.9–2.4 (2H, m), 5.16 (1H, d, J=5 Hz), 5.84 (1H, d, J=5 Hz), 6.92 (1H, s), 7.0–7.9 (4H, m)

EXAMPLE 12

Preparation of 7-[2-{N-(3-Pyridyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer).

To a suspension of 7-[2-{N-(3-pyridyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer) (2.7 g.) in methanol (40 ml.) was added conc. hydrochloric acid (1.09 ml.) with stirring at room temperature followed by stirring for 2 hours at the same temperature. The reaction mixture was separated by decantation into two groups, that is, a methanol layer and viscous precipitates. The methanol layer was treated with activated charcoal and concentrated and then the residue was dissolved in water. After the solution was adjusted to pH 3 to 4 with an aqueous solution of sodium bicarbonate, the precipitates are collected by filtration to give a powder of the title compound (0.6 g.). On the other hand, the viscous precipitates were dissolved in a mixture of methanol conc. hydrochloric acid and water and the solution was stirred for an hour at room temperature, treated with activated charcoal and then concentrated. The residue was dissolved in water and thereto was added an aqueous solution of sodium bicarbonate under cooling whereby the pH was adjusted to 3 to 4. The precipitates were collected by filtration to give a powder of the title compound (1.0 g.). Total Total yield: 1.6 g. mp. 180° to 210° C.

I.R. (Nujol): 3340, 3230, 1770, 1677, 1623, 1540 cm$^{-1}$

N.M.R. (DMSO-$d_6$+$D_2O$, δ): 3.7 (2H, broad s), 3.97 (3H, s), 4.3 (2H, broad s), 4.8 (2H, broad s), 5.20 (1H, d, J=5 Hz), 5.90 (1H, d, J=5 Hz), 6.97 (1H, s), 7.47 (1H, d, d, J=8, 4 Hz), 8.0–8.5 (2H, m), 8.85 (1H, d, J=2 Hz)

EXAMPLE 13

Preparation of 7-[2-{N-(2-Carboxyphenyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer)

7-[2-{N-(2-tert-Butoxycarbonylphenyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer) (2.0 g.) was added to a mixture of trifluoroacetic acid (7 ml.) and anisole (0.35 ml.) with stirring at about 10° C., followed by stirring for 1.5 hours at 5° to 10° C. and for an additional 15 minutes at room temperature. After concentration of the reaction mixture, to the residue were added methanol (30 ml.) and conc. hydrochloric acid (2.33 ml.). The resulting mixture was stirred for 1.5 hours at room temperature and concentrated and then the residue was shaken with a mixture of an aqueous solution of sodium bicarbonate and ethyl acetate. The aqueous layer (pH 7 to 8) was separated and thereto were added ethyl acetate and 10% hydrochloric acid with stirring whereby the pH was adjusted to 2 to 3. The resulting precipitates were filtered and redissolved in an aqueous solution of sodium bicarbonate. To the aqueous solution (150 ml.) was added ethyl acetate (300 ml.) and the mixture was acidified to pH 2 to 3 with 10% hydrochloric acid. The ethyl acetate layer was separated, washed with an aqueous solution of sodium chloride, dried and then concentrated. The residue was washed with diethyl ether to give the title compound (0.8 g.). mp 220° to 230° C. (dec.)

I.R. (Nujol): 3400–3100, 1782, 1680, 1538 cm$^{-1}$

N.M.R. (DMSO-$d_6$+$D_2O$, δ): 8.54 (1H, d, J=8 Hz), 7.99 (1H, d, J=8 Hz), 7.62 (1H, t, J=8 Hz), 7.20 (1H, t, J=8 Hz), 6.91 (1H, s), 5.89 (1H, d, J=5 Hz), 5.16 (1H, d, J=5 Hz), 4.74 (2H, s), 4.37, 4.22 (2H, ABq, J=13 Hz), 3.94 (3H, s), 3.75, 3.60 (2H, ABq, J=17 Hz)

EXAMPLE 14

The following compounds were prepared by procedures similar to those described in Examples 7 to 13.

(1) 7-[2-{N-(3-Chlorophenyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp. 191° to 195° C. (dec.)

I.R. (Nujol): 3300, 3200, 1775, 1680 cm$^{-1}$

N.M.R. (DMSO-$d_6$+$D_2O$, δ): 3.7 (2H, broad s), 3.90 (3H, s), 4.3 (2H, broad s), 4.7 (2H, broad s), 5.15 (1H, d, J=5 Hz), 5.83 (1H, d, J=5 Hz), 6.93 (1H, s), 7.0–7.9 (4H, m)

(2) 7-[2-{N-(2-Thiazolyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp. 180° to 185° C. (dec.)

I.R. (Nujol): 3330, 3230, 1780, 1680, 1630, 1550 cm$^{-1}$

N.M.R. (DMSO-$d_6$, δ): 3.74, 3.64 (2H, ABq, J=18 Hz), 3.95 (3H, s), 4.26, 4.35 (2H, ABq, J=14 Hz), 4.85 (2H, s), 5.18 (1H, d, J=5 Hz), 5.84 (1H, d, d, J=8, 5 Hz), 6.88 (1H, s), 7.26 (1H, d, J=3 Hz), 7.50 (1H, d, J=3 Hz), 9.80 (1H, d, J=8 Hz)

(3) 7-[2-{N-(2-Hydroxy-3,5-dichlorophenyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp. 161° to 170° C. (dec.)

I.R. (Nujol): 3300, 3200, 1775, 1675 cm$^{-}$

N.M.R. (DMSO-$d_6$, δ): 3.56, 3.76 (2H, ABq, J=18 Hz), 3.90 (3H, s), 4.20, 4.38 (2H, ABq, J=14 Hz), 4.73 (2H, s), 5.14 (1H, d, J=5 Hz), 5.80 (1H, d, d, J=8, 5 Hz), 6.84 (1H, s), 7.24 (1H, d, J=2 Hz), 7.80 (1H, d, J=2 Hz)

(4) 7-[2-{2-(2-Hydroxy-5-chlorobenzamido)ethoxyimino}-2-(2-aminothiazol-4-yl)acetamido]-3-(1-methyl-1H-tetrazol-5-yl)thiomethyl-3-cephem-4-carboxylic acid (syn isomer), mp. 220° to 230° C. (dec.)

I.R. (Nujol): 3330, 1789, 1678, 1640, 1595, 1540 cm$^{-1}$

N.M.R. (DMSO-$d_6$, δ): 9.56 (1H, d, J=9 Hz), 8.90 (1H, broad s), 7.91 (1H, d, J=2 Hz), 7.44 (1H, d, d, J=9, 2 Hz), 6.96 (1H, d, J=9 Hz), 6.82 (1H, s), 5.85 (1H, d, d, J=8, 5 Hz), 5.13 (1H, d, J=5 Hz), 4.6–4.0 (4H, m), 3.93 (3H, s), 3.1–3.9 (4H, m)

(5) 7-[2-{N-(2-Hydroxy-5-chlorophenyl)carbamoylmethoxyimino}-2-(2-aminothiazol-4-yl)acetamido]-cephalosporanic acid (syn isomer), mp>250° C.

I.R. (Nujol): 3330, 1777, 1738, 1670 cm$^{-1}$

N.M.R. (DMSO-$d_6$+$D_2O$, δ): 2.03 (3H, s), 3.45 3.62 (2H, ABq, J=14 Hz), 4.72, 4.97 (2H, ABq, J=14 Hz), 5.17 (1H, d, J=5 Hz), 5.87 (1H, d, J=5 Hz), 6.6–7.1 (3H, m), 8.00 (1H, d, J=2 Hz)

(6) 7-[2-{N-(3-Chlorophenyl)carbamoylmethoxyimino}-2-(2-aminothiazol-4-yl)acetamide]-3-(5-methyl-1,3,4-thiadiazol-2-yl)thiomethyl-3-cephem-4-carboxylic acid (syn isomer), mp 173° C. (dec.)

I.R. (Nujol): 3320, 1767, 1675 cm$^{-1}$

N.M.R. (DMSO-$d_6$+$D_2O$, δ): 2.70 (3H, s), 3.60, 3.77 (2H, ABq, J=18 Hz), 4.22, 4.48 (2H, ABq, J=14 Hz), 4.77 (2H, broad s), 5.20 (1H, d, J=5 Hz), 5.88 (1H, d, J=5 Hz), 6.93 (1H, s), 7.0–7.9 (4H, m)

(7) 7-[2-[2-[{3-(2-Chlorophenyl)-5-methylisoxazol-4-yl}carboxamido]ethoxyimino]-2-(2-aminothiazol-4-yl)acetamido]-3-(1,3,4-thiadiazol-2-yl)thiomethyl-3-cephem-4-carboxylic acid (syn isomer).

I.R. (Nujol): 3400–3100, 1770, 1650, 1520 cm$^{-1}$

N.M.R. (DMSO-$d_6$, δ): 3.17–3.87 (4H, m), 4.1 (2H, m), 4.45 (2H, q, J=14 Hz), 5.17 (1H, d, J=5 Hz), 5.80 (1H, d d, J=5.8 Hz), 6.80 (1H, s), 7.55 (4H, s), 9.50 (1H, d, J=8 Hz), 9.56 (1H, s)

EXAMPLE 15

Preparation of 7-[2-{N-(2-Hydroxy-5-chlorophenyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer)

To a mixture of 7-[2-{N-(2-hydroxy-5-chlorophenyl)-carbamoylmethoxyimino}-2-(2-formamidothiazol-4-yl)acetamido]cephalosporanic acid (syn isomer) (653 mg.), 1-methyl-1H-tetrazol-5-thiol (140 mg.) and sodium bicarbonate (190 mg.) in phosphate buffer (pH 6.4) (50 ml.) was stirred for 5 hours at 60° to 65° C. After cooling, the reaction mixture was washed with ethyl acetate and then thereto was added ethyl acetate. The mixture was adjusted to pH 2 with 10% hydrochloric acid and the ethyl acetate layer was separated, washed with water, dried over magnesium sulfate and then evaporated. The residue was pulverized with diethyl ether, washed with diethyl ether, collected by filtration and then dried to give the title compound (350 mg.).

I.R. (Nujol): 3250, 1780, 1680 cm$^{-1}$

N.M.R. (DMSO-$d_6$+$D_2O$, δ): 3.7 (2H, broad s), 3.92 (3H, s), 4.3 (2H, broad s), 4.8 (2H, broad s), 5.18 (1H, d, J=5 Hz), 5.87 (1H, d, J=5 Hz), 6.8–7.2 (2H, m), 7.57 (1H, s), 7.97 (1H, d, J=2 Hz), 8.53 (1H, s)

EXAMPLE 16

The following compounds were prepared by a procedure similar to that described in Example 15.

(1) 7-[2-(O,O-Diethylphosphono)methoxyimino-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3200, 1790, 1730, 1690 cm$^{-1}$ (2) 7-[2-{2-(O,O-Diethylphosphono)ethoxyimino}-2-(2-formamidothiazol-4-yl)acetamido]-3-(1-methyl-1H-tetrazol-5-yl)thiomethyl-3-cephem-4-carboxylic acid (syn isomer).

I.R. (Nujol): 1785, 1730, 1690 cm$^{-1}$ (3) 7-[2-{2-(O,O-Diethylphosphono)ethoxyimino}-2-(2-formamidothiazol-4-yl)acetamido]-3-(2-benzothiazolyl)-thiomethyl-3-cephem-4-carboxylic acid (syn isomer), mp. 132° to 150° C. (dec.).

(4) 7-[2-{N-(3-Pyridyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer).

I.R. (Nujol): 1780, 1680 cm$^{-1}$ (5) 7-[2-{N-(2-tert-Butoxycarbonylphenyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer), mp. 175° to 185° C. (dec.).

(6) 7-[2-{N-(3-Chlorophenyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3300, 1785, 1690 cm$^{-1}$ (7) 7-[2-{N-(2-Thiazolyl)carbamoylmethoxyimino}-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3250, 1785, 1740, 1700, 1670 cm$^{-1}$ (8) 7-[2-{N-(2-Hydroxy-3,5-dichlorophenyl)carbamoylmethoxyimino}-2-(2-formamidothiazol-4- yl)acetamido]-3-(1-methyl-1H-tetrazol-5-yl)thiomethyl-3-cephem-4-carboxylic acid (syn isomer).

(9) 7-[2-{2-(2-Hydroxy-5-chlorobenzamido)ethoxyimino}-2-(2-formamidothiazol-4-yl)acetamido]-3-(1-methyl-1H-tetrazol-5-yl)thiomethyl-3-cephem-4-carboxylic acid (syn isomer), powder.

I.R. (Nujol): 3220, 1797, 1697, 1650, 1595, 1535, 1470 cm$^{-1}$

(10) 7-[2-{N-(3-Chlorophenyl)carbamoylmethoxyimino}-2-(2-formamidothiazol-4-yl)acetamido]-3-(5-methyl-1,3,4-thiadiazol-2-yl)thiomethyl-3-cephem-4-carboxylic acid (syn isomer), mp 160° C. (dec.)

(11) 7-[2-{N-(2-Hydroxy-5-chlorophenyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp 165° to 175° C. (dec.)

(12) 7-[2-Phosphonomethoxyimino-2-(2-aminothiazol-4-yl)acetamido]-3-(1-methyl-1H-tetrazol-5-yl)thiomethyl-3-cephem-4-carboxylic acid (syn isomer), mp. 210° to 220° C. (dec.)

(13) 7-[2-{2-(O,O-Diethylphosphono)ethoxyimino}-2-(2-amonothiazol-4-yl)acetamido]-3-(1-methyl-1H-tetrazol-5-yl)thiomethyl-3-cephem-4-carboxylic acid. hydrochloride (syn isomer), mp 170° to180° C. (dec.)

(14) 7-[2-(2-Phosphonoethoxyimino)-2-(2-aminothiazol-4-yl)acetamido]-3-(1-methyl-1H-tetrazol-5-yl)thiomethyl-3-cephem-4-carboxylic acid (syn isomer), mp. 180° to 210° C. (dec.)

(15) 7-[2-(2-Phosphonoethoxyimino)-2-(2-aminothiazol-4-yl)acetamido]-3-(2-benzothiazolyl)thiomethyl-3-cephem-4-carboxylic acid (syn isomer), mp. 170° to 210° C. (dec.)

(16) 7-[2-{N-(3-Pyridyl)carbamoylmethoxyimino-2-(2-aminothiazol-4-yl)acetamido]-3-(1-methyl-1H-tetrazol-5-yl)thiomethyl-3-cephem-4-carboxylic acid (syn isomer), powder, mp. 180° to 210° C. (dec.)

(17) 7-[2-{N-(2-Carboxyphenyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp. 220° to 230° C. (dec.)

(18) 7-[2-{N-(3-Chlorophenyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp. 191° to 195° C. (dec.)

(19) 7-[2-{N-(2-Thiazolyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp. 180° to 185° C. (dec.)

(20) 7-[2-{N-(2-Hydroxy-3,5-dichlorophenyl)carbamoylmethoxyimino}-2-(2-aminothiazol-4-yl)acetamido]-3-(1-methyl-1H-tetrazol-5-yl)thiomethyl-3-cephem-4-carboxylic acid (syn isomer), mp. 161° to 170° C. (dec.)

(21) 7-[2-{2-(2-Hydroxy-5-chlorobenzamido)ethoxyimino}-2-(2-aminothiazol-4-yl)acetamido]-3-(1-methyl-1H-tetrazol-5-yl)thiomethyl-3-cephem-4-carboxylic acid (syn isomer), mp. 220° to 230° C. (dec.)

(22) 7-[2-{N-(3-Chlorophenyl)carbamoylmethoxyimino}-2-(2-aminothiazol-4-yl)acetamido]-3-(5-methyl-1,3,4-thiadiazol-2-yl)thiomethyl-3-cephem-4-carboxylic acid (syn isomer), mp 173° C. (dec.)

(23) 7-[2-[2-[{3-(2-Chlorophenyl)-5-methylisoxazol-4-yl}carboxamido]ethoxyimino]-2-(2-formamidothiazol-4-yl)acetamido]-3-(1,3,4-thiadiazol-2-yl)thiomethyl-3-cephem-4-carboxylic acid (syn isomer).

I.R. (Nujol): 3400–3100, 1780, 1660, 1540 cm$^{-1}$

(24) 7-[2-[2-[{3-(2-Chlorophenyl)-5-methylisoxazol-4-yl}carboxamido]ethoxyimino]-2-(2-aminothiazol-4-yl)acetamido]-3-(1,3,4-thiadiazol-2-yl)thiomethyl-3-cephem-4-carboxylic acid (syn isomer).

I.R. (Nujol): 3400–3100, 1770, 1650, 1520 cm$^{-1}$

EXAMPLE 17

A solution of 7-[2-(2-aminoethoxyimino)-2-(2-formamidothiazol-4-yl)acetamido]-3-(1,3,4-thiadiazol-2-yl)thiomethyl-3-cephem-4-carboxylic acid formate (syn isomer) (0.5 g.) and bis(trimethylsilyl)acetamido (1.5 g.) in dry tetrahydrofuran (10 ml) was stirred at 0° to 5° C. and thereto was added 3-(2-chlorophenyl)-5-methylisoxazole-4-carbonyl chloride (0.23 g.) The resulting mixture was stirred for 5 hours at 0° to 5° C. After the addition of water (20 ml) and ethyl acetate (20 ml) to the reaction mixture, the organic layer was separated. The organic layer was washed with a saturated aqueous solution of sodium chloride, dried over magnesium sulfate and then evaporated under reduced pressure to give 7-[2-[2-[{3-(2-chlorophenyl)-5-methylisoxazol-4-yl}carboxamido]ethoxyimino]-2-(2-formamidothiazol-4-yl)acetamido]-3-(1,3,4-thiadiazol-2-yl)thiomethyl-3-cephem-4-carboxylic acid (syn isomer) (0.4 g.)

I.R. (Nujol): 3400–3100, 1780, 1660, 1540 cm$^{-1}$

N.M.R. (DMSO-d$_6$, δ): 2.43 (3H, s), 3.17–3.73 (4H, m), 4.07 (2H, m), 4.42 (1H, q, J=13 Hz), 5.12 (1H, d, J=5 Hz), 5.78 (1H, dd, J=5 and 8 Hz), 7.38 (1H, s), 7.45 (4H, s), 8.47 (1H, s), 9.48 (1H, s), 9.52 (1H, d, J=8 Hz), 12.5 (1H, broad s).

What we claim is:

1. A compound of the formula:

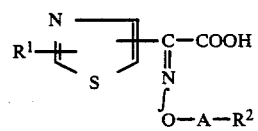

wherein

R$^1$ is amino or lower alkanoylamino;

R$^2$ is a group of the formula: —CONH—R$^5$ or —NHCO—R$^5$, wherein

R$^5$ is pyridyl; thiazolyl; or isoxazolyl having lower alkyl and halogen substituted phenyl, and A is lower alkylene, or a non-toxic salt thereof.

2. The compound of claim 1 wherein

R$^1$ is amino or lower alkanoylamino; and

R$^2$ is a group of the formula: —CONH—R$^5$, wherein R$^5$ is pyridyl or thiazolyl.

3. The compound of claim 2, which is 2-[N-(3-Pyridyl)carbamoylmethoxyimino]-2-(2-formamidothiazol-4-yl)-acetic acid (syn isomer).

4. The compound of claim 2, which is 2-[N-(2-Thiazolyl)carbamoylmethoxyimino]-2-(2-formamidothiazol-4-yl) acetic acid (syn isomer).

* * * * *